United States Patent
Palti

(10) Patent No.: US 8,019,414 B2
(45) Date of Patent: Sep. 13, 2011

(54) TREATING CANCER USING ELECTROMAGNETIC FIELDS IN COMBINATION WITH OTHER TREATMENT REGIMENS

(75) Inventor: Yoram Palti, Haifa (IL)

(73) Assignee: Novocure Ltd., Haifa (IL)

( * ) Notice: Subject to any disclaimer, the term of this patent is extended or adjusted under 35 U.S.C. 154(b) by 740 days.

(21) Appl. No.: 11/695,176

(22) Filed: Apr. 2, 2007

(65) Prior Publication Data

US 2007/0239213 A1    Oct. 11, 2007

Related U.S. Application Data

(60) Provisional application No. 60/744,295, filed on Apr. 5, 2006.

(51) Int. Cl.
*A61N 1/18* (2006.01)
(52) U.S. Cl. .............................. 607/3; 607/75
(58) Field of Classification Search .................. None
See application file for complete search history.

(56) References Cited

U.S. PATENT DOCUMENTS

| | | |
|---|---|---|
| 2,220,269 A | 11/1940 | Patzold et al. |
| 3,991,770 A | 11/1976 | LeVeen |
| 4,016,886 A | 4/1977 | Doss et al. |
| 4,121,592 A | 10/1978 | Whalley |
| 4,263,920 A | 4/1981 | Tasto et al. |
| 4,467,809 A | 8/1984 | Brighton |
| 4,472,506 A | 9/1984 | Liburdy |
| 4,622,952 A | 11/1986 | Gordon |
| 4,626,506 A | 12/1986 | Zimmermann et al. |
| 4,676,258 A | 6/1987 | Inokuchi et al. |
| 4,822,470 A | 4/1989 | Chang |
| 4,846,178 A | 7/1989 | Fuxue et al. |
| 4,846,196 A | 7/1989 | Wiksell et al. |
| 4,923,814 A | 5/1990 | Marshall |
| 4,936,303 A | 6/1990 | Derwiler et al. |
| 4,971,991 A | 11/1990 | Umemura et al. |
| 5,099,756 A | 3/1992 | Franconi et al. |
| 5,158,071 A | 10/1992 | Umemura et al. |
| 5,236,410 A | 8/1993 | Granov et al. |
| 5,269,304 A | 12/1993 | Matthews |

(Continued)

FOREIGN PATENT DOCUMENTS

EP    0 330 797 A2    9/1989

(Continued)

OTHER PUBLICATIONS

Hofmann et al., "Electronic Genetic-Physical and Biological Aspects of Cellular Electomanipulation", IEEE Eng. in Med. and Biology Mag., Dec. 1986, p. 6-23, New York.

(Continued)

*Primary Examiner* — Carl H. Layno
*Assistant Examiner* — Jon-Eric C. Morales
(74) *Attorney, Agent, or Firm* — Proskauer

(57) ABSTRACT

Chemotherapeutic treatment for certain cancers may be combined with low intensity, intermediate frequency alternating electric fields that are tuned to a particular type of target cell. When the tuned fields were combined with Paclitaxel, Doxorubicin or Cyclophosphamide, excellent results were obtained against human breast cancer cells (MDA-MB-231) and non-small cell lung (H1299) carcinomas in culture. More specifically, cell proliferation inhibition similar to that obtained by drug alone was reached by exposure to the combined treatment at drug concentrations between one and two orders of magnitude lower than for drug-only regimens of treatment.

23 Claims, 17 Drawing Sheets

U.S. PATENT DOCUMENTS

| | | | |
|---|---|---|---|
| 5,312,813 | A | 5/1994 | Costerton et al. |
| 5,386,837 | A | 2/1995 | Sterzer |
| 5,389,069 | A | 2/1995 | Weaver |
| 5,441,532 | A | 8/1995 | Fenn |
| 5,441,746 | A | 8/1995 | Chagnon |
| 5,468,223 | A | 11/1995 | Mir |
| 5,606,971 | A | 3/1997 | Sarvazyn |
| 5,674,267 | A | 10/1997 | Mir et al. |
| 5,718,246 | A | 2/1998 | Vona |
| 5,807,257 | A | 9/1998 | Bridges |
| 5,964,726 | A | 10/1999 | Korenstein et al. |
| 5,976,092 | A | 11/1999 | Chinn |
| 5,984,882 | A | 11/1999 | Rosenchein et al. |
| 6,027,488 | A | 2/2000 | Hofmann et al. |
| 6,043,066 | A | 3/2000 | Mangano et al. |
| 6,055,453 | A | 4/2000 | Hofmann et al. |
| 6,068,650 | A | 5/2000 | Hofmann et al. |
| 6,096,020 | A | 8/2000 | Hofmann et al. |
| 6,319,901 | B1 | 11/2001 | Bernard et al. |
| 6,366,808 | B1 | 4/2002 | Schroeppel et al. |
| 6,413,255 | B1 | 7/2002 | Stern |
| 6,447,499 | B2 | 9/2002 | Gray |
| 6,856,839 | B2 | 2/2005 | Litovitz |
| 6,868,289 | B2 | 3/2005 | Palti |
| 7,016,725 | B2 | 3/2006 | Palti |
| 7,089,054 | B2 | 8/2006 | Palti |
| 7,136,699 | B2 | 11/2006 | Palti |
| 7,146,210 | B2 | 12/2006 | Palti |
| 7,333,852 | B2 | 2/2008 | Palti |
| 7,467,011 | B2 | 12/2008 | Palti |
| 7,519,420 | B2 | 4/2009 | Palti |
| 7,565,205 | B2 | 7/2009 | Palti |
| 7,565,206 | B2 | 7/2009 | Palti |
| 2002/0077676 | A1* | 6/2002 | Schroeppel et al. ............ 607/75 |
| 2002/0193832 | A1 | 12/2002 | Gray |
| 2002/0193833 | A1 | 12/2002 | Dimmer et al. |
| 2003/0060856 | A1 | 3/2003 | Chornenky et al. |
| 2003/0150372 | A1 | 8/2003 | Palti |
| 2003/0191506 | A1 | 10/2003 | Shloznikov |
| 2004/0068297 | A1 | 4/2004 | Palti |
| 2004/0176804 | A1 | 9/2004 | Palti |
| 2005/0209640 | A1 | 9/2005 | Palti |
| 2005/0209641 | A1 | 9/2005 | Palti |
| 2005/0209642 | A1 | 9/2005 | Palti |
| 2005/0240173 | A1 | 10/2005 | Palti |
| 2005/0240228 | A1 | 10/2005 | Palti |
| 2006/0149337 | A1* | 7/2006 | John ............................... 607/45 |
| 2006/0149341 | A1 | 7/2006 | Palti |
| 2006/0167499 | A1 | 7/2006 | Palti |
| 2006/0233867 | A1 | 10/2006 | Palti |
| 2006/0237019 | A1 | 10/2006 | Palti |
| 2006/0241547 | A1 | 10/2006 | Palti |
| 2006/0276858 | A1 | 12/2006 | Palti |
| 2006/0282122 | A1 | 12/2006 | Palti |
| 2007/0028310 | A1 | 2/2007 | Palti |
| 2007/0033660 | A1 | 2/2007 | Palti |
| 2007/0225766 | A1 | 9/2007 | Palti |
| 2007/0239213 | A1 | 10/2007 | Palti |
| 2008/0221630 | A1 | 9/2008 | Palti |
| 2008/0319372 | A1 | 12/2008 | Palti |
| 2009/0043346 | A1 | 2/2009 | Palti |
| 2009/0076366 | A1 | 3/2009 | Palti |

FOREIGN PATENT DOCUMENTS

| | | |
|---|---|---|
| EP | 1 916 013 | 4/2008 |
| GB | 1 419 660 A1 | 12/1975 |
| GB | 2 026 322 A1 | 2/1980 |
| GB | 2 043 453 A1 | 10/1980 |
| JP | 2004 081133 | 3/2004 |
| WO | WO 01/60994 | 8/2001 |
| WO | 02/39786 | 5/2002 |
| WO | 2006/085150 | 8/2006 |
| WO | 2006/131816 | 12/2006 |

OTHER PUBLICATIONS

Berg et al., "Electric Field Effects on Bilogical Membranes:Electoincorporation and Electofusion",Ettore Maj Inter. Science, 1987,p. 135-166,vol. 32,Phys. Science, New York.

Kirson et al., "Disruption of Cancer Cell Replication by Alternating Electric Fields", Cancer Research 64, May 2004, p. 3288-3295, Haifa, Israel.

Asbury et al., "Trapping of DNA in Nonuniform Oscillating Electric Fields", Biophysical Journal, Feb. 1998, p. 1024-1030, vol. 74,Seattle, WA.

Giladi et al., Microbial Growth Inhibition by Alternating Electric Fields, Antimicrobial Agents and Chemotherapy, Oct. 2008, p. 3517-3522.

Janigro et al., Alternating current electrical stimulation enhanced chemotherapy: a novel strategy to bypass multidrug resistance in tumor cells, BMC Cancer 2006, 6:72.

* cited by examiner

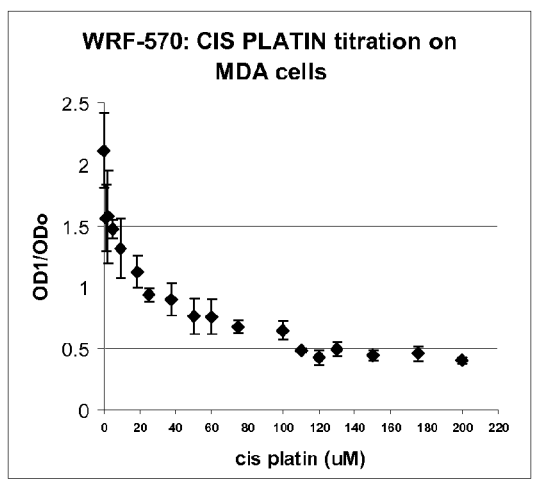
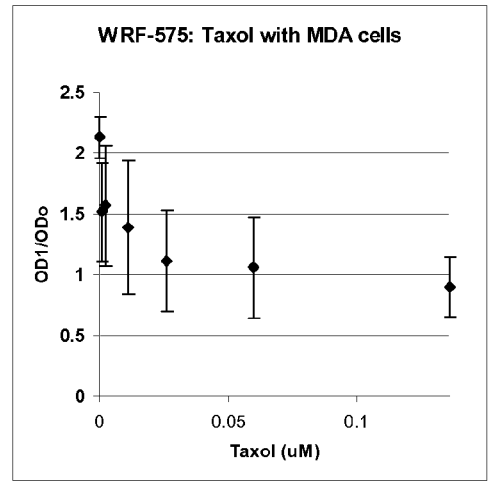
FIG. 2A  FIG. 2B
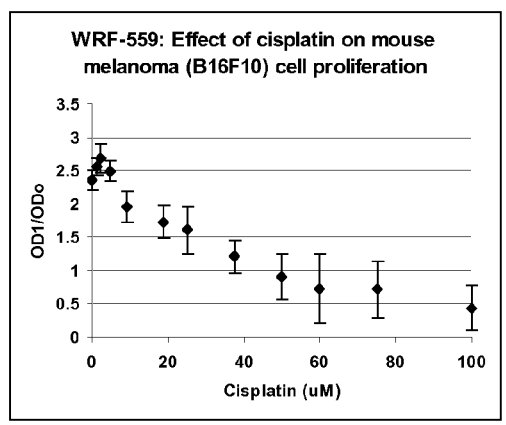
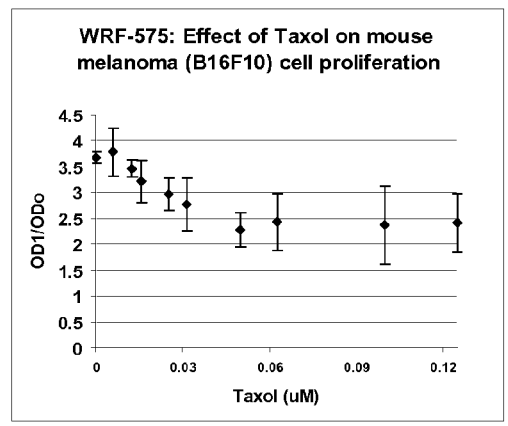
FIG. 3A  FIG. 3B

TREATING CANCER USING ELECTROMAGNETIC FIELDS IN COMBINATION WITH OTHER TREATMENT REGIMENS

CROSS REFERENCE TO RELATED APPLICATIONS

This application claims the benefit of U.S. provisional application 60/744,295, filed Apr. 5, 2006.

BACKGROUND

As described in U.S. Pat. Nos. 6,868,289 and 7,016,725 each of which is incorporated herein by reference, and in U.S. patent application Ser. Nos. 11/111,439 (filed Apr. 21, 2005 and published as US2005/0209642) and Ser. No. 11/537,026 (filed Sep. 29 2006), each of which is incorporated herein by reference, intermediate frequency (100-300 kHz) alternating electric fields, (referred to herein as "TTFields") damage as well as inhibit the growth of numerous types of cancer cells in vitro as well as a number of malignancies in vivo. The efficacy of the treatment is enhanced by sequentially applying fields of varying directions and by the use of special insulated electrodes.

TTFields act by two mechanisms of action: First, they disrupt the normal polymerization-depolymerization process of the spindle microtubules during mitosis. Secondly, they cause a physical disruption of cells towards the end of cytokinesis by producing a unidirectional force on all charge, polar and polarizable intracellular constituents, pushing them towards the narrow neck between the two daughter cells. See Kirson, E. D., et al., *Disruption of cancer cell replication by alternating electric fields*, Cancer Res., 2004. 64(9): p. 3288-95, which is incorporated herein by reference.

Drugs and radiation therapy are more conventional approaches to treating cancer. One example is Cisplatin or cis-diamminedichloroplatinum(II) (CDDP), which is a platinum-based chemotherapy drug used to treat various types of cancers, including sarcomas, some carcinomas (e.g. small cell lung cancer and ovarian cancer), lymphomas and germ cell tumors. It was the first member of its class, which now also includes carboplatin and oxaliplatin. Another example is Paclitaxel, more commonly referred to by the trade name Taxol®, which is a member of the larger family of compounds known as taxanes. Currently, Paclitaxel is used in the treatment of breast, ovarian, certain non-small-cell lung cancers, and Kaposi's sarcoma.

SUMMARY OF THE INVENTION

Chemotherapeutic treatment for certain cancers are combined with low intensity, intermediate frequency alternating electric fields that are tuned to a particular type of target cell to inhibit the growth of the cancer cells. In many cases, the resulting cell proliferation inhibition is significantly higher than the inhibition obtained by drug-only regimens of treatment.

BRIEF DESCRIPTION OF THE DRAWINGS

FIGS. 2A and 2B depict the results of cytotoxicity calibration experiments for Cisplatin and Taxol, respectively, on MDA-231 cells.

FIGS. 3A and 3B depict the results of cytotoxicity calibration experiments for Cisplatin and Taxol, respectively, on B16F10 cells.

FIG. 14 is a cross-sectional illustration of a skin patch incorporating the apparatus of FIG. 5 and for placement on a skin surface for treating a tumor or the like.

FIG. 15 is a cross-sectional illustration of the insulated electrodes implanted within the body for treating a tumor or the like.

DETAILED DESCRIPTION OF THE PREFERRED EMBODIMENTS

Figure 1:
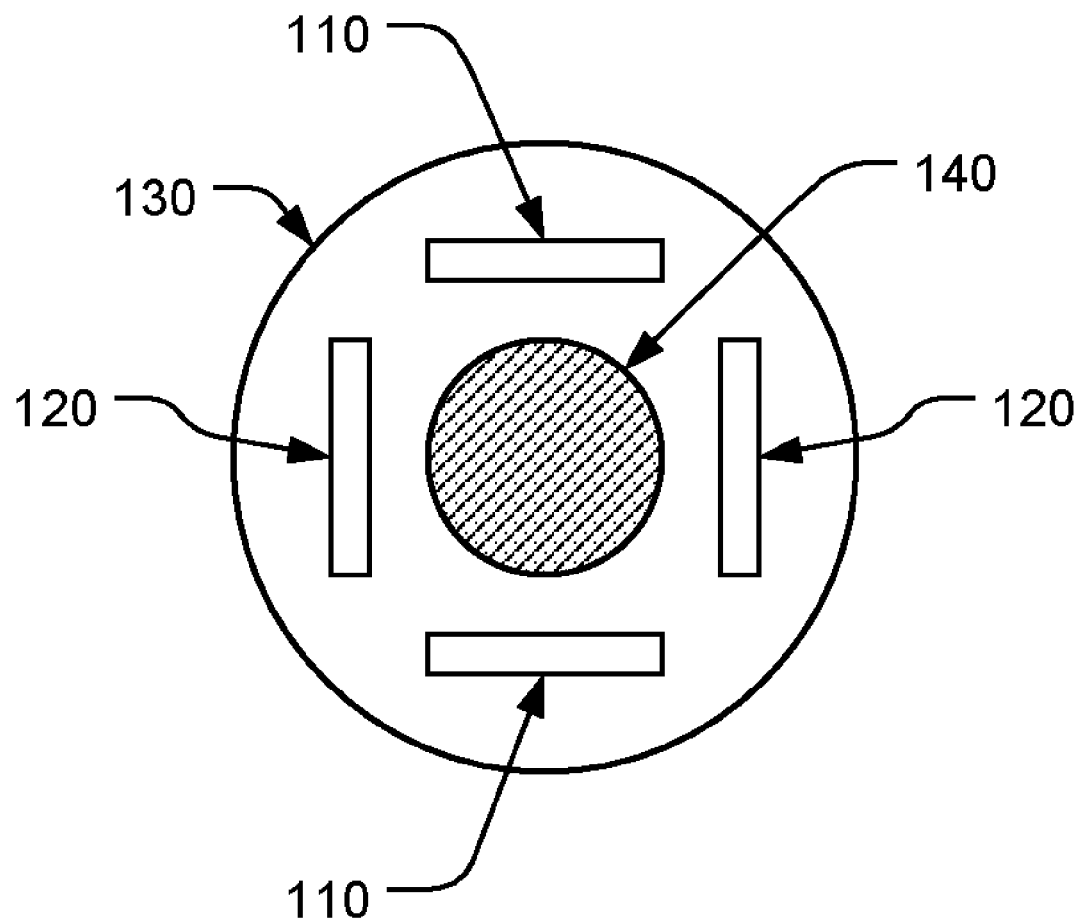
FIG. 1 depicts an electrodes arrangement for applying TTFields to an in vitro specimen.

When used as the only treatment modality, the therapeutic efficacy of TTFields was found to be high and the therapeutic index extremely high (few or no side effects), however, treatment duration was relatively long and the required field intensities were relatively high. In order to improve the treatment efficacy, the effects of combining TTFields with other treatment modalities was tested. It was hypothesized that such a combination would be beneficial regardless of whether the mechanism of action of the two (or more) modalities was similar or different, and experiments were conducted to test this hypothesis. The results of those experiments are described below. In each of the experiments, a TTField treatment protocol previously shown to be effective was selected, and the efficacy of the TTFields and each agent alone were compared to the efficacy of the combined treatment with TTFields and each of the agents.

First Set of Experiments

In a first set of experiments, TTFields were applied (with the field direction alternating between two directions) to human breast cancer (MDA231) and mouse melanoma (B16F10) cells in culture, both with and without a chemotherapeutic agent. Taxol and Cisplatin were selected as the agents because they have different mechanisms of action.

The MDA-231 and B16F10 cells were obtained from ATCC (USA). Both types of cells were cultured in DMEM+ 10% FCS media (Biological Industries Ltd., Israel) in $CO_2$ incubator (5% $CO_2$) at 37° C. Cell resuscitation was done using Trypsin/EDTA solution (0.25%/0.02%, Biological Industries Ltd., Israel). The experiments were performed in 35 mm Petri dishes (NUNC, USA). Cisplatin and Taxol were obtained from Sigma (USA). A cell proliferation assay kit was obtained from Biological Industries Ltd., Israel.

Cells, grown in 25 $cm^2$ cell culture flasks, were removed using Trypsin/EDTA solution (0.25%/0.02%), diluted with complete media to final concentration of $75 \times 10^3$ cells per ml. 200 μl of diluted suspension were placed as a drop in the centre of 35 mm Petri dish and incubated for 24 hours. The initial cell number was measured as a light absorption by formazan produced by cells during 2 hours using the XTT method and expressed as $OD_0$. (XTT is sodium 3'-[1-(phenyl-amino-carbonyl)-3,4-tetrazolium]-bis (4-methoxy-6-nitro)-benzene solfonic acid hydrate. XTT is cleaved to formazan (absorbs at 450-500 nm) by the "succinate-tetrazolium reductase" system of the respiratory chain of the mitochondria and is active only in viable cells. Therefore, the amount of formazan dye ($A_{450\ nm}$) formed directly correlates to the number of metabolically active cells in culture. The XTT assay is widely used for the measurement of cell proliferation in response to growth factors, cytokines, mitogens, nutrients, anti-cancer drugs and physiological mediators.)

The media in the Petri dish was replaced by fresh media (3 ml with or without Taxol or Cisplatin), thermo-couples were placed at the center, and the dish cover was replaced by one with attached electrodes. Cell samples without TTField treatment were placed in $CO_2$ incubator at 37° C. for 24 hours, while TTField treated samples were placed in $CO_2$ incubator at 25° C., also for 24 hours. Final incubation temperature of TTField treated samples was 37±0.7° C. due to heating induced by TTFields (as measured by inserted thermo-couples). At the end of 24 hour treatment, the final cell number was measured as an absorption by formazan produced by cells during 2 hours using XTT method and expressed as $OD_1$.

The rate of cell proliferation was calculated as a ratio of the final cell number to the initial cell number ($OD_1/OD_0$). An $OD_1/OD_0$ ratio of 1 means that there is no increase in cell number, i.e., a complete cell proliferation arrest is achieved. The change in the cell number proliferation rate was calculated as $(OD_1/OD_0-1)_{EXPERIMENT}/(OD_1/OD_0-1)_{CONTROL}$.

In order to evaluate the ability of treated cells to recover, the cells were incubated in normal media after treatment removal for additional 24 hours, and the number of cells was measured as an absorption by formazan produced by cells during 2 hours using XTT method and expressed as $OD_2$. The rate of cell proliferation $OD_2/OD_1$ was calculated as a ratio of final cell number (after the additional incubation period) $OD_2$ per initial cell number (before the additional incubation period) $OD_1$.

For those samples that were subjected to TTFields, two-directional 200 kHz sinusoidal TTFields were generated by an appropriate waveform generator and an amplifier. The output of the amplifier was switched between two pairs of outputs every 250 mSec, with the outputs connected to two pairs of electrodes, insulated by a high dielectric constant ceramic (e.g., PMN-PT, EDO Corporation, Utah), positioned in the Petri dish as depicted in FIG. 1. Field intensity in the medium surrounding the cells was measured to be approximately 7V/cm. Thus, each pair of parallel electrodes was activated at a duty-cycle of 50% (250 mSec ON-250 mSec OFF) such that when one pair was ON, the other pair was OFF.

Before the main experiments were conducted, calibration experiments were performed to determine the doses of Cisplatin and Taxol that should be used in the main experiments for the two representative cell cultures studied. The purpose of these calibration experiments was to find the dosage of the respective drug that, taken alone (i.e., without TTFields), provided a cytotoxicity such that about 50% of the cells are killed within the 24 hour study period. FIGS. 2A and 2B depict the results of these calibration experiments for Cisplatin and Taxol, respectively, on MDA-231 cells; and FIGS. 3A and 3B depict the results of these calibration experiments for Cisplatin and Taxol, respectively, on B16F10 cells. On the basis of the calibration experiment, a drug concentration of 15 μM was chosen for the main experiment with Cisplatin and, and a drug concentration of 0.05 μM was chosen for the main experiment with Taxol.

After the drug concentrations were selected (based on the calibration experiments), the main experiments were performed to determine the effects of (a) each drug taken alone; (b) two-directional TTFields taken alone; and (c) both drugs and two-directional TTFields.

Figure 4:
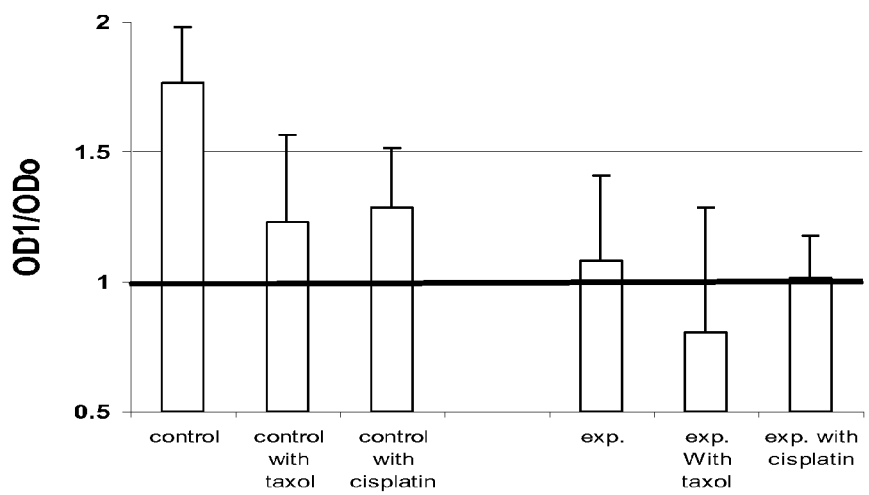
FIG. 4 depicts the cell proliferation measured in an experiment on human breast cancer (MDA-231) cells.

FIG. 4 depicts the results of the main experiment on human breast cancer (MDA-231) cell proliferation, as measured by the XTT assay. It can be seen see that Taxol (0.05 μM) and Cisplatin (15 μM) alone reduced cell proliferation by 70% and 63% respectively as compared with the control. The TTFields alone (labeled "exp.") reduced cell proliferation by 89%. The combination of TTFields with Taxol (labeled "exp. with Taxol") or Cisplatin (labeled "exp. with Cisplatin") led to an increase in proliferation arrest. In the case of Cisplatin there was complete cell proliferation arrest $OD_1\sim OD_0$, and when Taxol was used in combination with TTFields there was an absolute reduction of the number of cells indicating that on top of complete proliferation arrest (about 40% of the cells died under the influence of the combined treatment).

Figure 5:
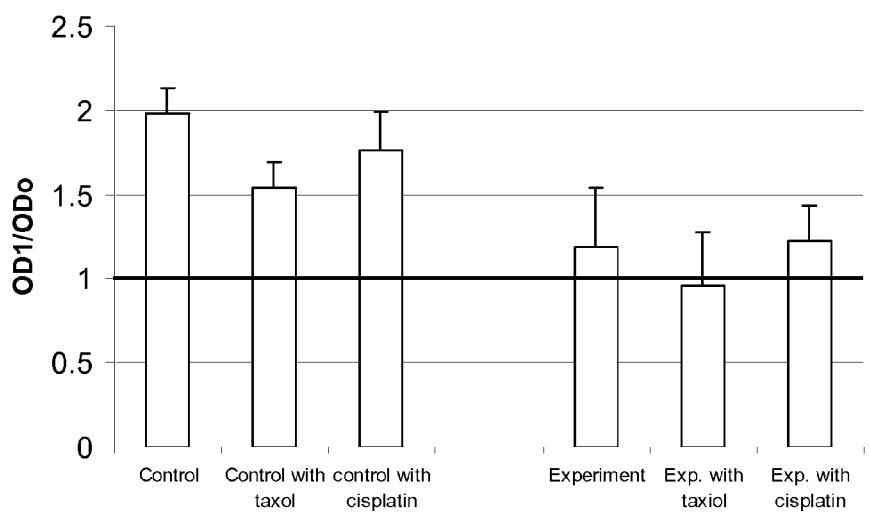
FIG. 5 depicts the cell proliferation measured in an experiment on mouse melanoma (B16F10) cells.

FIG. 5 depicts the results of the main experiment on mouse melanoma (B16F10) cell proliferation, as measured by the XTT assay. It can be seen that Taxol (0.05 μM) (labeled "control with Taxol") and Cisplatin (15 μM) (labeled "control with Cisplatin") alone reduced cell proliferation to a lesser extent than the combined effect of either drug in combination with the TTFields (labeled "exp. with Taxol" and "exp. with Cisplatin", respectively).

Figure 6:
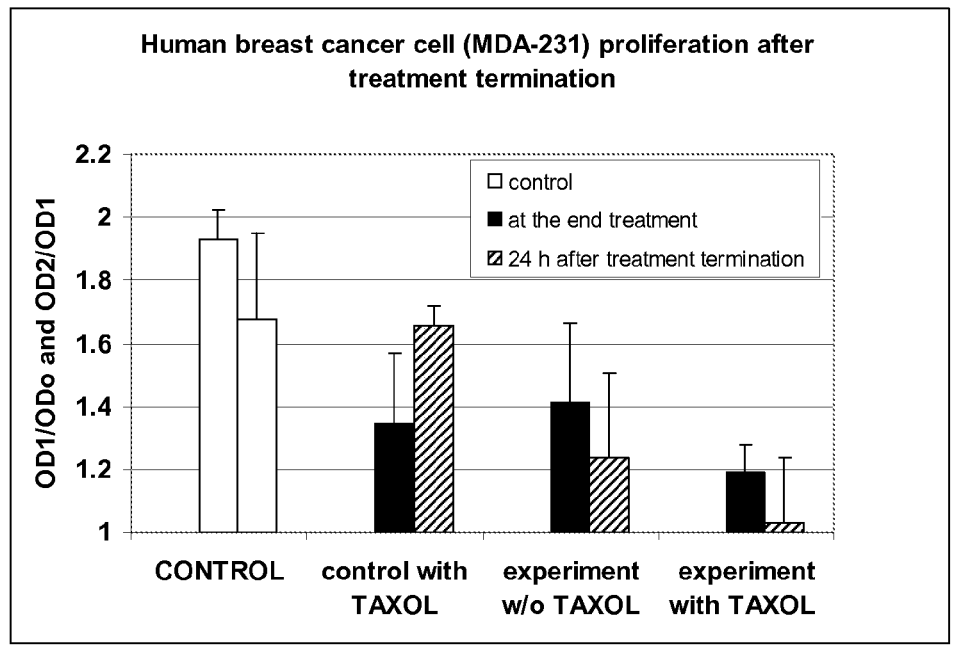
FIG. 6 depicts the recovery of the rate of cell proliferation 24 hours after treatment was stopped.

FIG. 6 depicts the recovery of the rate of cell proliferation that was observed 24 hours after treatment removal, which can serve as an additional index of the treatment potency. FIG. 6 contains four pairs of bars. Within each pair, the left bar represents $OD_1/OD_0$, and the right bar represents $OD_2/OD_1$. The results demonstrate that there is complete recovery of proliferation after Taxol removal (see the large $OD_2/OD_1$ bar labeled "control with Taxol"). In marked contrast, there is no cell recovery after either TTFields treatment alone or after combined Taxol and TTField treatment (see the small $OD_2/OD_1$ bars labeled "experiment w/o Taxol" and "experiment with Taxol").

Second Set of Experiments

In a second set of experiments, TTFields were applied (with the field direction alternating between two directions) to human breast cancer (MDA-MB-231) and non-small cell lung carcinoma (H1299) cells in culture, both with and without each of three chemotherapeutic agents (Paclitaxel, Doxorubicin and Cyclophosphamide) in various concentrations Human breast cancer (MDA-MB-231) and human non-small cell lung cancer (H1299) cells were obtained from ATCC (USA). The cells were cultured in DMEM+10% FCS media (Biological Industries Ltd., Israel) in a 5% $CO_2$ incubator at 37° C. The chemotherapeutic agents: Taxol (Paclitaxel), adriamycin (Doxorubicin) and Cyclophosphamide were obtained from Sigma, USA. The stock solution of Paclitaxel was prepared in DMSO (Sigma USA) at concentration of 5 mM. The stock solutions of Doxorubicin and Cyclophosphamide were prepared in phosphate buffered saline at concentrations of 8.5 mM and 3.0 M respectively. All stock solutions were stored at –20° C. and were freshly diluted with media shortly before their introduction to the cultured cells.

In the experimental set up, cells grown in 25 $cm^2$ cell culture flasks were removed using trypsin/EDTA (0.25%/0.02%) solution (Biological Industries Ltd., Israel), diluted with the media described above, to a final concentration of $100\times10^3$ cells per ml. 200 μl of diluted suspension were placed as a drop at the centre of 35 mm Petri dishes (NUNC, USA). After the dishes were incubated for 2 hours at 37° C., to allow for cell attachment, 1.5 ml of complete media was added and cells were incubated for an additional 22 hours (pre-incubation).

After pre-incubation, the initial cell number was estimated using standard XTT method (Cell proliferation assay Kit, Biological Industries Ltd., Israel) by measuring the light absorption by formazan, produced by cells during a period of 2 hours, and expressed as $OD_0$. The media in the Petri dishes was then replaced by fresh media (3 ml), with or without a chemotherapeutic agent. Temperature was continuously measured by a thermocouple (Omega, UK) placed at the center of the dish. As illustrated in FIG. 1, two pairs of electrodes 110, 120, insulated by a high dielectric constant ceramic (PMN-PT, EDO Corporation, Utah), connected to sinusoidal waveform generator—TTField generator (NovoCure Ltd., Haifa, Israel), were positioned in all Petri dishes 130 (including controls) so as to alternately generate electric fields in two different directions around the cultured cells 140.

Control cell dishes that did not receive TTFields treatment, were placed in a $CO_2$ incubator at 37° C. for 24 hours while TTFields treated dishes were placed in a $CO_2$ incubator in which temperature was controlled such that the final incubation temperature of treated dishes was 37±0.5° C. At the end of 24 hours treatment, the cell number was estimated again using the XTT method and expressed as $OD_1$ (the light absorption by formazan produced by cells during a period of 2 hours). The rate of cell proliferation was expressed as the $OD_1/OD_0$ ratio. The $OD_1/OD_0$ ratio for untreated cells was in the range of 2.0±0.2 for both cell lines studied, i.e. the cell number doubled during the 24 hour incubation. Treatment efficacy is expressed as the change in the rate of cell proliferation, presented as a % of control, calculated for each experiment by the following equation:

$$(OD_1/OD_0)_{EXPERIMENT}*100\%/(OD_1/OD_0)_{CONTROL}.$$

To optimize the field effect, two fields of perpendicular direction were generated sequentially in an alternating pattern by switching the output of the amplifier between the two pairs of electrodes every 250 ms. The electric field intensity in the culture medium was measured using a probe consisting of two 0.25 mm diameter insulated wires with exposed tips 1 mm apart, which was dipped in the culture media at the centre of the Petri dish. A high-input impedance differential amplifier translated the alternating potential difference amplitude into a corresponding DC voltage that was recorded. Note that field intensities used throughout this specification are expressed in peak voltage amplitude difference per centimeter distance (V/cm).

Four different runs were conducted in conjunction with each chemotherapeutic agent: untreated control, treatment with either TTFields alone, treatment with one of the chemotherapeutic agents alone, and combined TTField—chemo treatment.

The Chou and Talley method for assessing the combined effect of multiple drugs was used for the drug—TTFields combinations. TTField intensity replaced the classical concentration variable in the analyses. Dose-response curves were generated for TTFields and each drug separately to determine the median effect plots. Variable ratios of drug concentrations—TTFields intensities were used to determine the Combination indexes (Cist):

$$CI=(C_{A,x}/Ix_{x,A})+(B_{B,x}/IC_{x,B})$$

Where: $C_{A,X}$ and $C_{B,x}$ are the concentrations (intensities) of treatment A and treatment B used in combination to achieve a predetermined x % effect. $IC_{x,A}$ and $IC_{x,B}$ are the corresponding concentrations (intensities) for any single agent to achieve the same effect. In all cases herein, A represents TTFields and B represents the chemotherapeutic drug.

This analysis allows drugs with different mechanisms of action to be assessed. A CI<1 denotes synergy (more than additive), a CI of 1 reflects summation (additive), and a CI>1 indicates antagonism (less than additive).

Isobologram analyses, for evaluation of the nature of interaction of two agents, were performed as follows: The concentrations (intensities) of agent A and B required to produce a defined single-agent effect of, for example, $IC_{50}$, $IC_{x,A}$ and $IC_{x,B}$, are plotted on the x and y axes in a two-coordinate plot, corresponding to $(C_A, 0)$ and $(0, C_B)$, respectively. The line connecting these two points is the line of additivity. The concentrations (intensities) of the two agents used in combination to provide the same selected level of effect denoted as point $(C_A, C_B)$, are introduced on the same plot. Synergy, additivity, or antagonism are indicated when the point ($C_A$, $C_B$) is located below, on, or above the line, respectively.

Results for Human Breast Cancer (MDA-MB-231)

Figure 7:
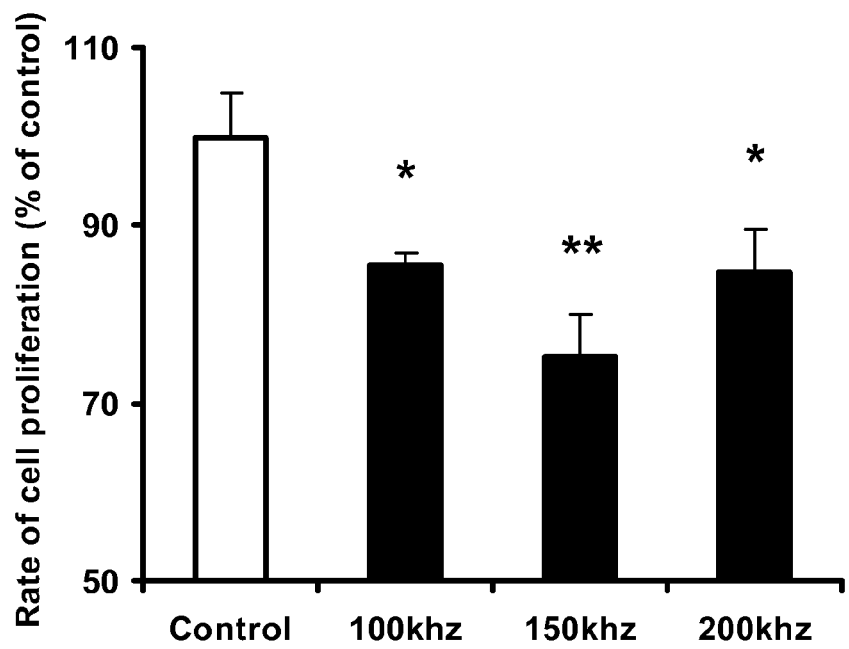
FIG. 7 depicts experimental results that show the frequency dependence of the TTFields anti-proliferation efficacy for human breast cancer (MDA-231) cells.

Since the sensitivity of different cell types to the TTFields frequency is different, an initial round of experiments was run to determine which frequency is most effective for each type of target cell. FIG. 7 depicts the results of those initial experiments, and shows the frequency dependence of the TTFields anti-proliferation efficacy for human breast cancer cells (MDA-MD-231). The data indicates a peak effectiveness at 150 kHz. Note that in the initial experiments, the TTField intensity was kept constant at 1.75 V/cm at all frequencies. Each point represents mean values±SEM of 18-36 samples, and all effects were statistically significant. In FIG. 7, * indicates a student's t test, P<0.01 relative to the control, and ** indicates a student's t test, P<0.01 relative to the experiments at 100&200 kHz.

A second round of experiments was then performed to determine the proliferation rate of ER-negative MDA-MB-231 cells (as % of control) after 24 hour exposure to Paclitaxel, Doxorubicin and Cyclophosphamide alone and in combination with TTFields at different intensities. FIGS. 8A-8D depict the results of these experiments.

Figure 8A:
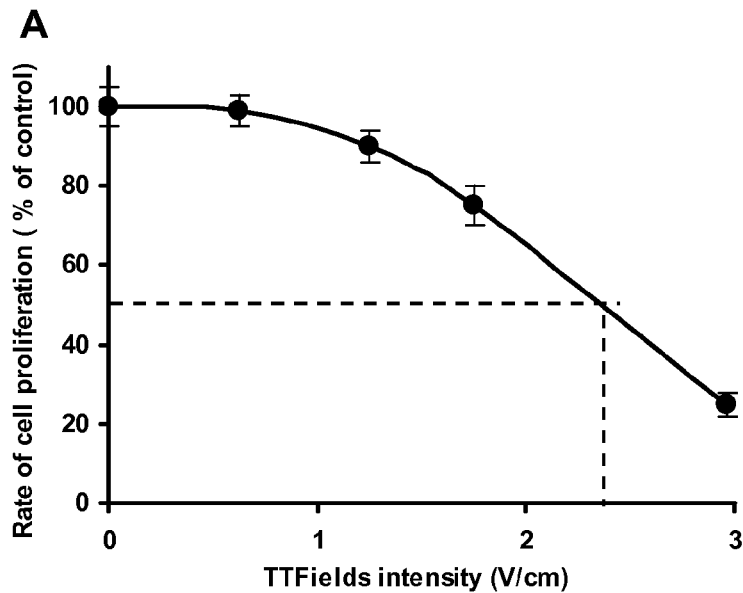
FIG. 8A depicts the measured relationship between TTFields intensity and cell proliferation rate for different field intensities for MDA-231 cells.

FIG. 8A depicts the measured relationship between TTFields intensity, and cell proliferation rate at field intensities of: 0.63, 1.25, 1.75 and 2.95 V/cm, when the field was applied alone (i.e., without any drugs) at the preselected frequency of 150 kHz. At the lowest field intensity of 0.63 V/cm there was no significant change in the proliferation rate (1.0±3.0%). At TTFields intensities of 1.25, 1.75 and 2.95 V/cm there was a significant decrease in the cell proliferation rate: 10±3%, 26±4% and 75±5%, respectively. The TTFields intensity required for complete proliferation arrest, i.e. a 50% decrease in the proliferation rate, was calculated from the slope of the curve to be 2.35 V/cm. In FIG. 8A, the symbols represent average values of 18 samples obtained from three experiments, and the bars represent mean values±SEM.

Figure 8B:
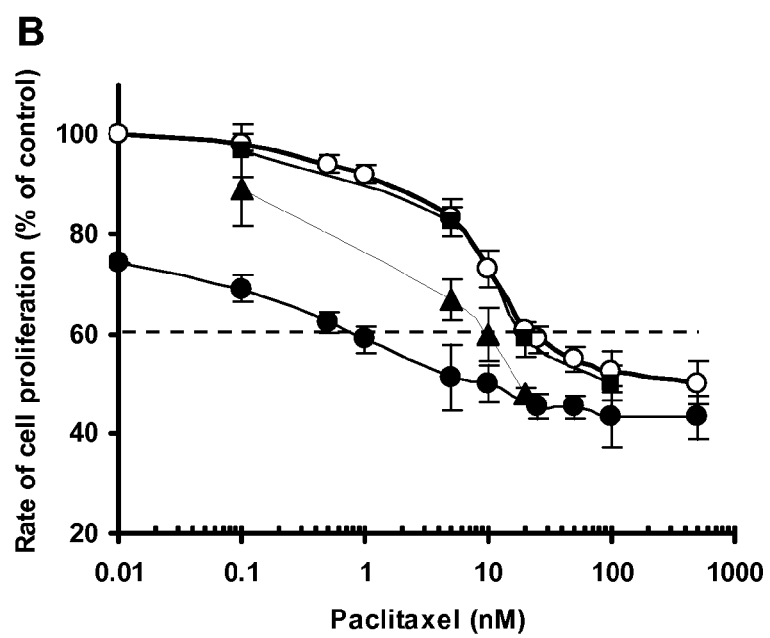
FIG. 8B depicts the dose-response curve for MDA-231 cell line subjected to increasing concentrations of Paclitaxel, alone and in combination with TTFields of different intensities.
Figure 8C:
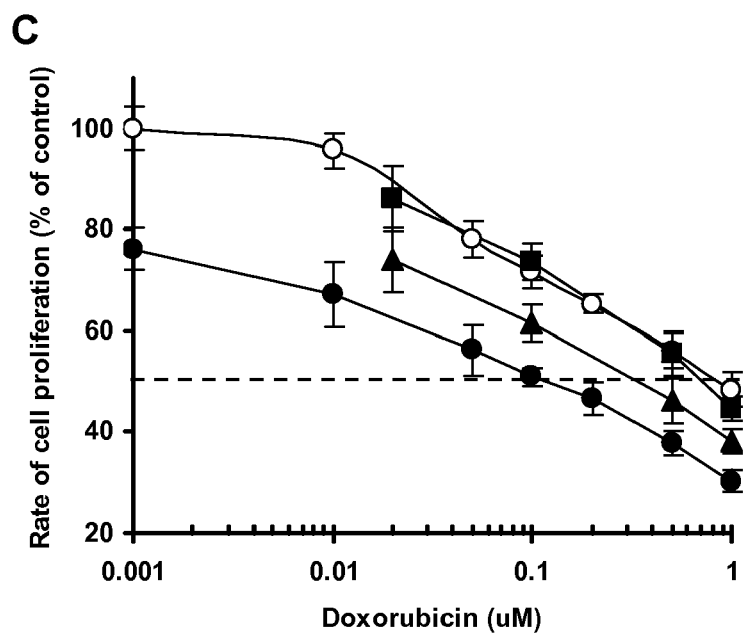
FIG. 8C depicts the dose-response curve for MDA-231 cell line subjected to increasing concentrations of Doxorubicin, alone and in combination with TTFields of different intensities.
Figure 8D:
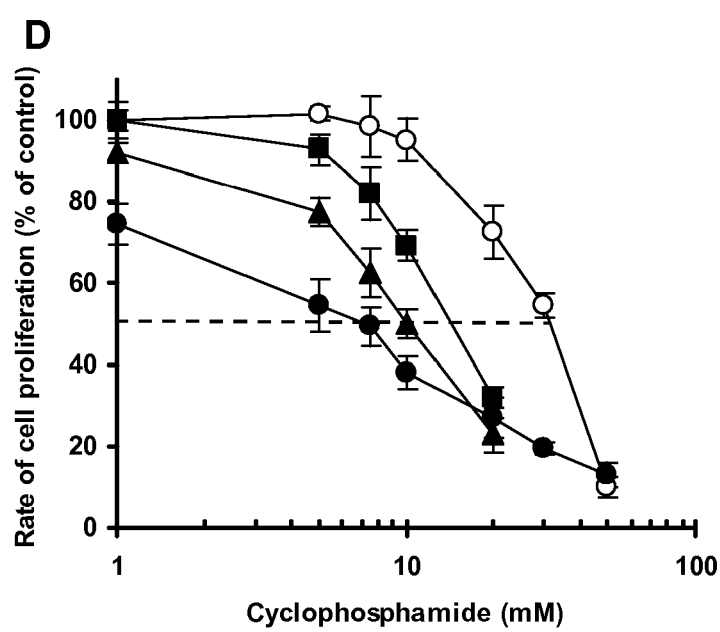
FIG. 8D depicts the dose-response curve for MDA-231 cell line subjected to increasing concentrations of Cyclophosphamide, alone and in combination with TTFields of different intensities.

Note that in FIGS. 8B-8D, data points with an open circle "?" represent the drug alone; the squares "|" represent the drug in combination with TTFields of 0.625 V/cm; the triangles "?" represents the drug in combination with TTFields of 1.25 V/cm; and the closed circles "?" represent the drug in combination with TTFields of 1.75 V/cm. Each point represents mean values±SEM of 18 to 36 replicate measurements.

FIG. 8B depicts the dose-response curve for MDA-MB-231 cell line subjected to increasing concentrations of Paclitaxel, in the range of 0.01-500 nM, both alone and in combination with TTFields of different intensities. A steep decrease in the cell proliferation rate is observed for the drug-only treatment when Paclitaxel concentration increases from 1.0 to 100 nM. At concentrations above 100 nM the proliferation rate stabilizes around the 50% level (e.g. complete arrest of cell proliferation without induction of cell death at this point in time). The dashed horizontal line represents a 60% of cell proliferation rate. (Note the inverse relationship between the rate of cell proliferation and the inhibitory effect of treatment, i.e., a 40% cell proliferation rate is equivalent to a 60% inhibition.)

It can be seen that low intensity TTFields (0.625 V/cm), in combination with Paclitaxel, have the same effect on cell proliferation rate as Paclitaxel alone at all Paclitaxel concentrations. In contrast, the combination of Paclitaxel and TTFields of higher intensities (1.25 and 1.75 V/cm) leads to a statistically significant (ANOVA, P<0.05) additional decrease in cell proliferation rate. The increase in cell growth inhibition by Paclitaxel, with and without TTFields, levels off at high Paclitaxel concentrations.

FIG. 8C depicts the dose-response curve for MDA-MB-231 cell line subjected to increasing concentrations of Doxorubicin, both alone and in combination with TTFields of different intensities. For the drug-only treatment, it is apparent that cell proliferation rate decreases with increase in Doxorubicin concentration until complete arrest (50% inhibition) is obtained at a concentration of about 1 μM. The dashed line represents 50% decrease in cell proliferation rate (i.e., 50% inhibition).

Once again, low intensity TTFields (0.625 V/cm) had no significant effect on cell proliferation when applied both alone and in combination with all concentrations of Doxorubicin. The combination of TTFields of higher intensities (1.25 and 1.75 V/cm) with Doxorubicin results in a statistically significant (ANOVA, P<0.05) anti-proliferation effect which is added to the one obtained by the drug alone. This enhanced inhibition is observed throughout the Doxorubicin concentration range used in the experiments. The concentrations of Doxorubicin required to reach complete arrest of cell proliferation (50% inhibition) during combined treatment is 0.41 μM and 0.22 μM for 1.25 V/cm and 1.75 V/cm TTFields respectively.

FIG. 8D depicts the dose-response curve for MDA-MB-231 human cell line subjected to increasing concentrations of Cyclophosphamide, alone, and in combination with TTFields of different intensities. In the absence of TTFields, Cyclophosphamide concentrations of up to 10 mM produce no significant changes in proliferation rate. Higher concentrations result in precipitous drop in the dose-response curve, and complete arrest of cell proliferation (50% inhibition) is seen at 30.0 mM of Cyclophosphamide. (The dashed line represents 50% inhibition.) Higher concentrations result in a further reduction of the number of cells.

The combined effect of Cyclophosphamide and TTFields has an additional anti-proliferation effect which becomes apparent even at the lowest concentrations used (statistically significant, ANOVA, P<0.05). The concentrations of Cyclophosphamide required to reach complete cell proliferation arrest (50% inhibition), during combined treatment are: 15.2 mM, 10.0 mM and 6.2 mM for 0.63 V/cm, 1.25 V/cm and 1.75 V/cm TTFields intensities, respectively. These values compare to 30 mM for complete cell proliferation arrest with the drug alone.

The results depicted in FIGS. 8A-D are for the cell proliferation rate at the end of 24 hours of treatment. However, the induction of cell damage may take 3-4 days due to accumulation of the damaged structures or molecules and the induction of cell suicidal pathway—apoptosis, and necrosis. Therefore another set of experiments was performed to compare the number of viable cells in culture along a period of 72 hours, when one set of cells was treated continuously for the entire 72 hour period by TTFields alone, drugs alone, or drugs in combination with TTFields, while the other was treated only for 24 hours and thereafter incubated under normal conditions for 48 hours.

Figure 9A:
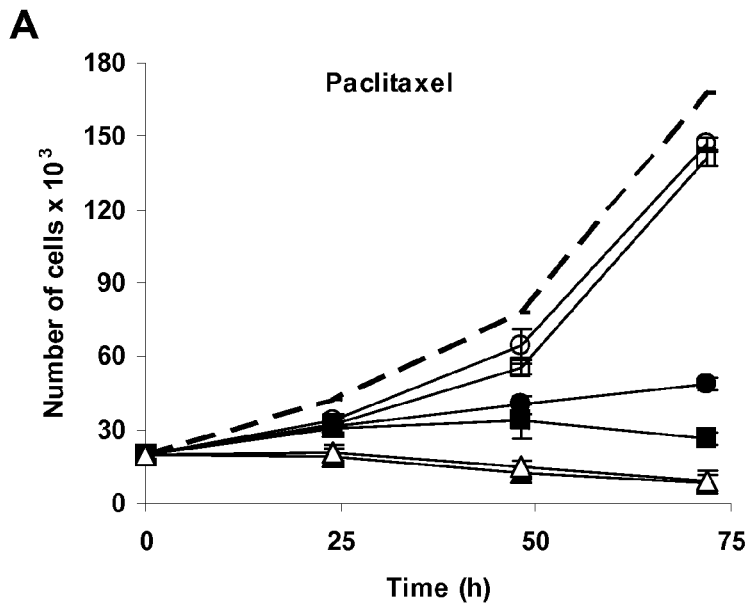
FIGS. 9A, 9B and 9C depict the results of experiments on ER-negative MDA-231 cells exposed to TTFields and three different chemotherapeutic agents for different durations.
Figure 9B:
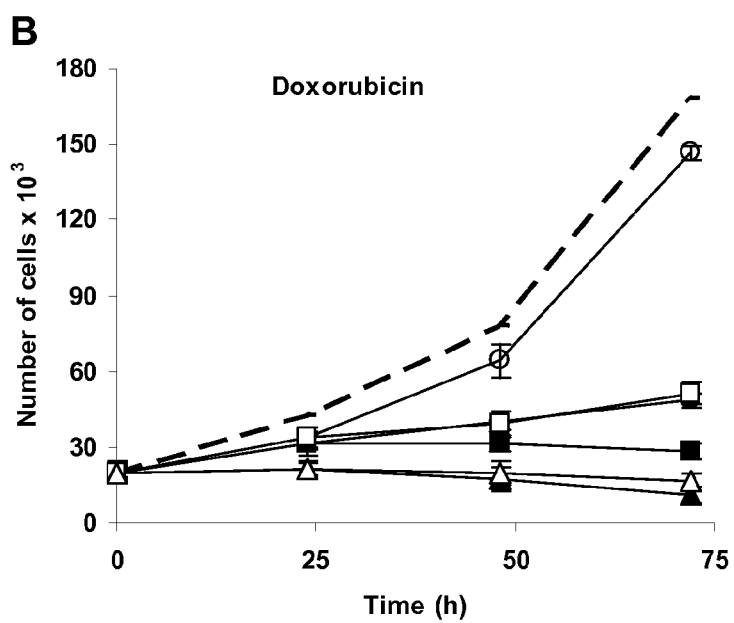
Figure 9C:
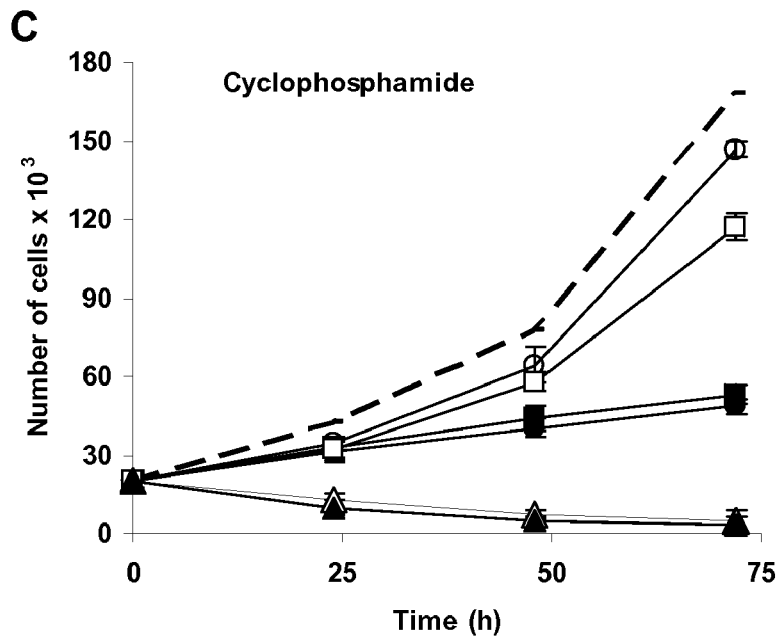

FIGS. 9A, 9B and 9C depict the results of these 72 hour experiments on ER-negative MDA-MB-231 cells exposed to TTFields and three different chemotherapeutic agents for different durations. In all three of those figures, the dashed line represents the untreated control, the open symbols represent 24 hour treatment, and the filled symbols represent 72 hour treatment, as summarized below in Table 1. Each point represents mean values±SEM of 24 replicate measurements obtained from 4 experiments.

TABLE 1

| ? Treatment with TTFields alone for 1 day | ? Treatment with TTFields alone for 3 days |
|---|---|
| ? Treatment with drug alone for 1 day | ⎪ Treatment with drug alone for 3 days |
| ? combined treatment for 1 day | ? combined treatment for 3 days |

FIG. 9A depicts the data for 12.5 nM Paclitaxel and 1.75 V/cm TTFields, both individually and combined, for both 24 and 72 hour treatment regimens. It is apparent that when cells are treated with for 24 hours with the TTFields alone (?) or the Paclitaxel alone (?) a similar reduction in proliferation rate and the corresponding cell number is obtained at the end of treatment (approx. 27±3%, lower than control). Subsequently, complete recovery of cell proliferation rate is seen; with the cell number approximately doubling every 24 hours of incubation. (A) 24-72 hours treatment with TTFields and Paclitaxel. When treatment is continued for an additional period of 48 hours, for TTFields alone (?) the cell number increases at a low rate (1.29 times per 24 h), while for Paclitaxel alone (⎪) proliferation completely stops during second day of treatment and the cell number is reduced during the third day. Combined treatment with TTFields and Paclitaxel for both 24 hours (?) and 72 hours (?) leads to induction of cell death already during the first 24 hours, with cell count continuing to fall throughout the 72 hours period even in the case (?) when the treatment is no longer being applied during the last 48 hours.

FIG. 9B depicts the data for 0.1 µM Doxorubicin and 1.75 V/cm TTFields, both individually and combined, for both 24 and 72 hour treatment regimens. It is apparent that treatment for 24 hours with the Doxorubicin alone (?) leads at the end of treatment to a reduction in cell number by 26±4% as compared to the control. During the following 48 hours, a slow increase in cell number is observed. Treatment for 72 hours by TTFields alone (?) shows almost exactly the same cell count profile. In contrast during a 72 hour long treatment with Doxorubicin (⎪) there is a complete arrest of cell division at the end of the second day and a small reduction in cell number after an additional 24 hours of treatment. The combined treatment of cells with both TTFields and Doxorubicin (?) leads to complete halt of cell division after first 24 hours. Induction of cell death is seen already at this point of time and continues during following 48 hours (even after the treatment is not being applied). A 72 hour long treatment period (?) results in an effect that is roughly similar to the 24 hour treatment (?).

FIG. 9C depicts the data for 20 mM Cyclophosphamide and 1.75 V/cm TTFields, both individually and combined, for both 24 and 72 hour treatment regimens. This figure shows that when cells are treated with the Cyclophosphamide alone for 24 hours (?) a reduction in cell number is obtained (approx. 27±2%). Cessation of the treatment at this point (after 24 hours) leads to almost complete recovery of the cell proliferation such that their number approximately doubles every 24 hours. Treatment by either Cyclophosphamide alone (⎪) or TTFields alone (?) for a period of 72 hours results in a linear relatively slow increase in the cell number. The combined treatment with both TTFields and Cyclophosphamide for either 24 hour (?) or 72 hour (?) period leads to a marked induction of cell death. After 24 hours the cell count is 40±3% lower as compared to their number before treatment initiation. At the end of 72 hours there is almost complete loss of cells.

Figure 9D:
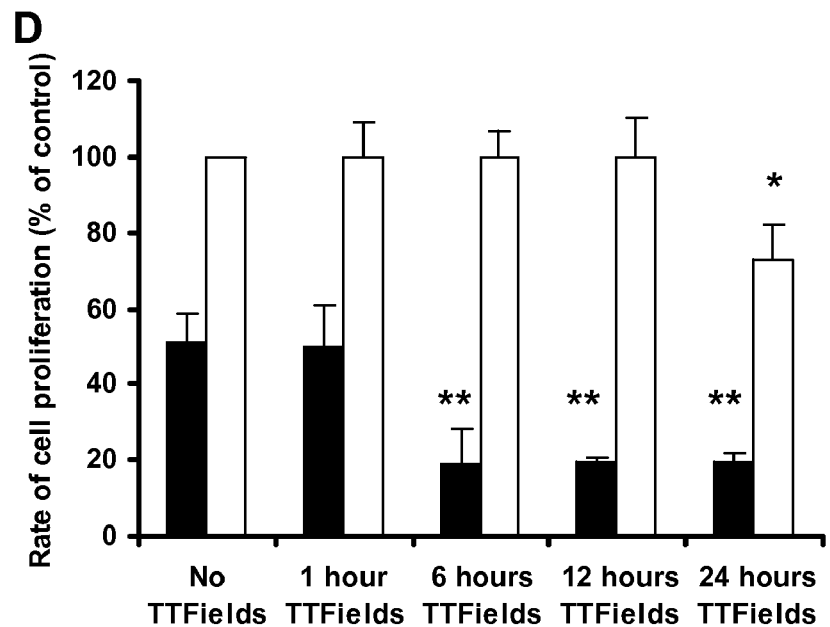
FIG. 9D illustrates the impact of how long the TTFields are applied when TTFields are used alone and in combination with Cyclophosphamide.

FIG. 9D illustrates the impact of how long the TTFields are applied when 1.75 V/cm TTFields are used alone (open columns) and when 1.75 V/cm TTFields are used in combination with 30 mM Cyclophosphamide (solid columns). The data indicates that when TTFields are used alone, short duration treatment of 12 hours or less is ineffective, but the 24 hour long treatment is effective (as are treatments for longer durations, as evidenced by the filled circles "?" in FIGS. 9A, 9B & 9C). In contrast, when the TTFields are combined with Cyclophosphamide (filled columns), the treatment is not effective when the TTFields are applied for 1 hour, but becomes fully effective when the TTFields are applied for 6 hours or more. This behavior may indicate a specific interaction between the two agents (see the discussion below). Note that in FIG. 9D, each column represents mean values±SEM of 18 replicate measurements obtained from 3 experiments. * $P<0.01$, student's t test relative to control. ** $P<0.01$, student's t test relative to Cyclophosphamide alone.

Results for Non-Small Cell Lung Carcinoma (H1299)

For human non-small cell lung cancer (H1299). Initial testing indicated that the TTFields are most effective at a frequency of 200 kHz. As a result, 200 kHz was selected for used in subsequent experiments to measure the effects of 24 hour exposure to Paclitaxel, Doxorubicin, and Cyclophosphamide alone and in combination with TTFields at different intensities.

Figure 10A:
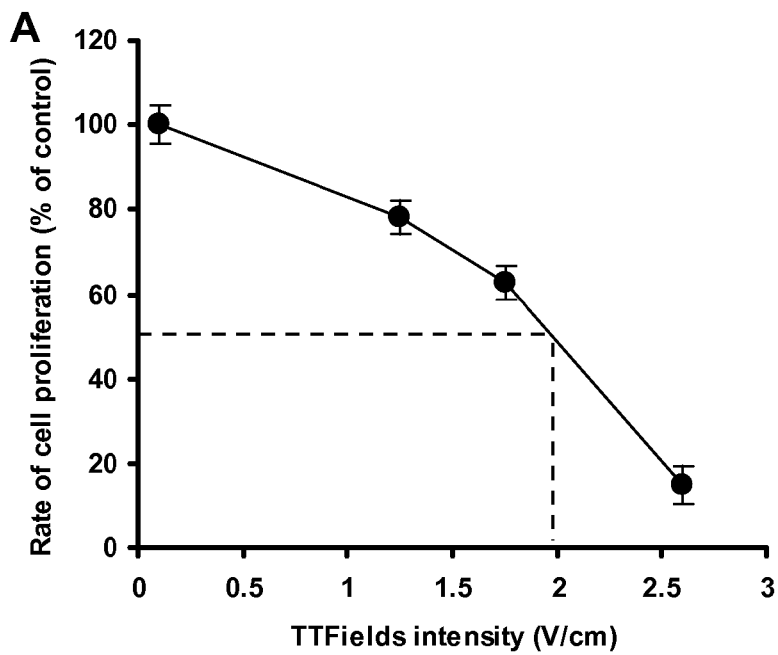
FIG. 10A depicts the relationship between the intensity of the 200 kHz TTFields (applied alone) and the cell proliferation rate for non-small cell lung carcinoma.

FIG. 10A depicts the relationship between the intensity of the 200 kHz TTFields (applied alone) and the non-small cell lung carcinoma cell proliferation rate. It is seen that cell proliferation decreases as TTFields intensity is increased. The intensity of TTFields required for complete proliferation arrest (a 50% decrease in the rate of cell proliferation), as calculated from the slope of the curve, is 2.0 V/cm. In FIG. 10A, the symbols represent average values of 18 samples obtained from three experiments and the bars represent ±SEM.

Figure 10B:
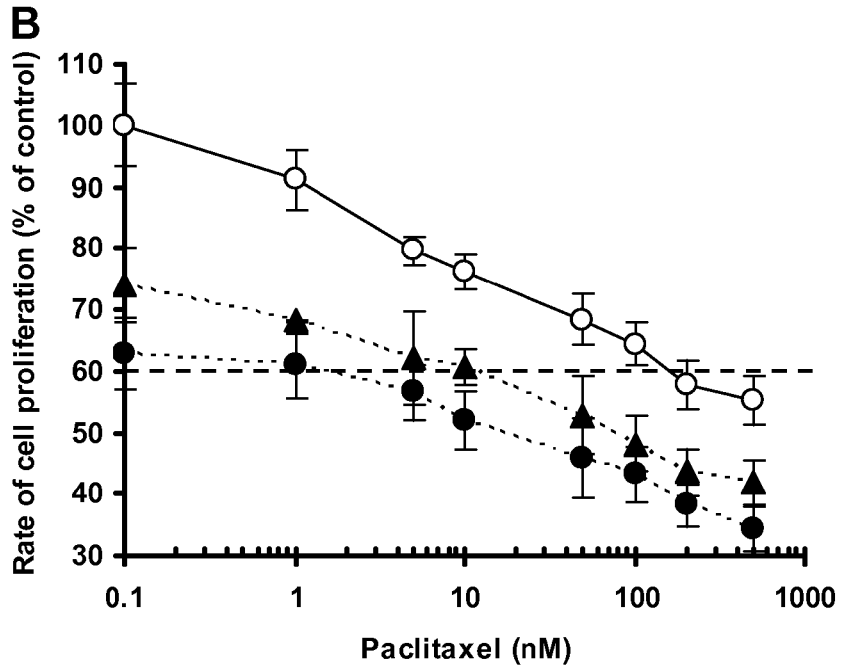
FIG. 10B depicts the dose-response curve for H1299 cell line, subjected to increasing concentrations of Paclitaxel, and in combination with TTFields.

FIG. 10B depicts the dose-response curve for H1299 cell line, subjected to increasing concentrations of Paclitaxel alone (?), and in combination with TTFields (?,?), as a % of control. For Paclitaxel alone, a steep decrease in cell proliferation rate is observed when Paclitaxel concentrations increase from 1.0 to 200 nM. At concentrations above 200 nM the proliferation rate reaches 55%, i.e. almost complete arrest of cell proliferation. The combined effect of Paclitaxel and TTFields of 1.25 V/cm (?) and 1.75 V/cm (?) intensities leads to a significant additional decrease in cell proliferation rate at all the concentrations studied. At the higher concentrations of Paclitaxel, when in combination with TTFields, cell death is induced. This effect that is not observed when Paclitaxel was used alone at concentrations up to 500 µnM. In this figure, each point represents mean values±SEM of 24 to 32 replicate measurements, and the dashed line represents 60% of cell proliferation rate (i.e., 40% inhibition).

Discussion of Results

The experimental results demonstrate that in general TTFields have either additive or synergistic effects with Paclitaxel, Doxorubicin and Cyclophosphamide for treatment of breast carcinoma and non-small cell carcinoma of the lung. As these three drugs are known to have different pharmacological mechanisms of action, it is not surprising that the details of the nature of their combined efficacy with the TTFields differ.

Paclitaxel is among the most commonly used microtubule-disrupting agents for the treatment of late-stage human breast cancer. Mechanistically, it exerts its anticancer actions primarily through disturbing the disassembly of microtubules, consequently resulting in mitotic arrest and cell death. This mechanism is similar to that reported for TTFields. The observed results show that TTFields enhance the anti-proliferation effect of Paclitaxel on both human breast cancer and non-small cell lung cancer cells, as explained above in connection with FIGS. 8 and 10.

The combination indexes (CI) obtained for human breast cancer (MDA-MB-231) and human non-small cell lung carcinoma (H1299) cells treated with different drugs in combination with TTFields of various intensities are summarized below in Table 2. It is seen that the combined effects of Paclitaxel, like the other agents, vary from additivity to synergism as can be deduced from the fact that the values of all the calculated Combination Indexes in Table 2 are less than 1.

TABLE 2

| TTFields intensity (V/cm) | Combination index | | | |
|---|---|---|---|---|
| | MDA-MB-231 cells | | | H1299 cells |
| | Paclitaxel $CI_{40}$ | Doxorubicin $CI_{50}$ | Cyclophosphamide $CI_{50}$ | Paclitaxel $CI_{40}$ |
| 0.625 | — | — | 0.74 | — |
| 1.25 | 0.97 | 0.99 | 0.84 | 0.73 |
| 1.75 | 0.86 | 0.98 | 0.95 | 0.98 |

Note that for Paclitaxel, the combination indexes for 60% proliferation rate equivalent to 40% inhibition level ($CI_{40}$) was used instead of the more commonly used $CI_{50}$, because the effects approach saturation above this level.

Figure 11A:
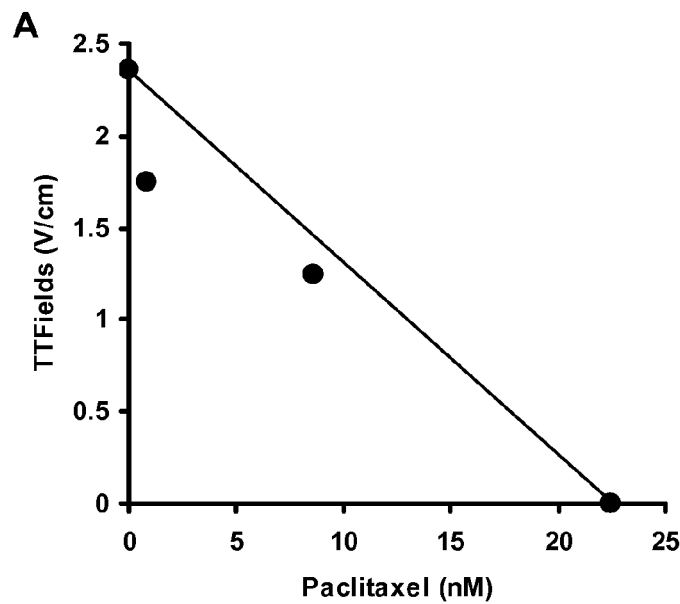
FIG. 11A is an Isobolographic plot for Paclitaxel at different concentrations and TTFields at different intensities on MDA-231 cells.
Figure 11B:
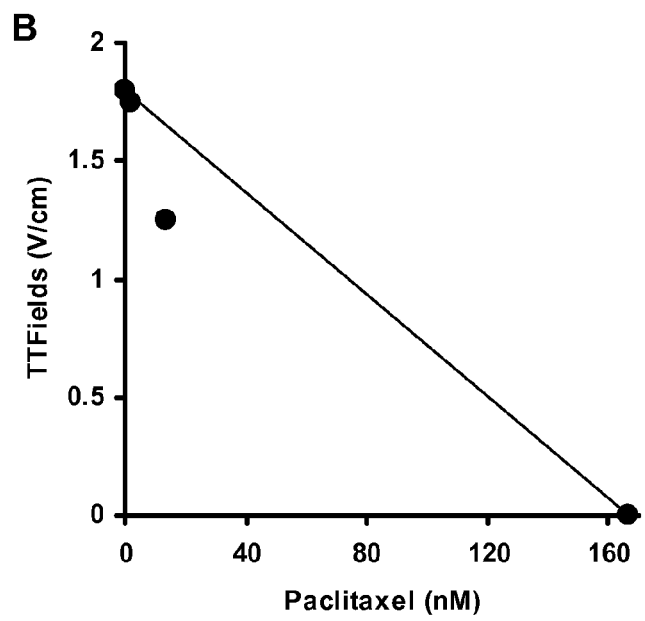
FIG. 11B is an Isobolographic plot for Paclitaxel at different concentrations and TTFields at different intensities on H1299 cells.

The combined effects of combination of TTFields of different intensities with chemotherapeutic agents of different concentrations can also be evaluated by means of isobolographic analysis. FIG. 11A is an Isobolographic plot for Paclitaxel at different concentrations and TTFields at different intensities on breast carcinoma MDA-MB-231; and FIG. 11B is an Isobolographic plot for Paclitaxel at different concentrations and TTFields at different intensities on non-small lung carcinoma H1299 cells. Synergism at the low concentrations is demonstrated by the fact that the data points fall below the isobole line. In FIGS. 11A and 11B, the two points on the axes represent the 40% response levels for Paclitaxel alone and TTFields alone.

Figure 11C:
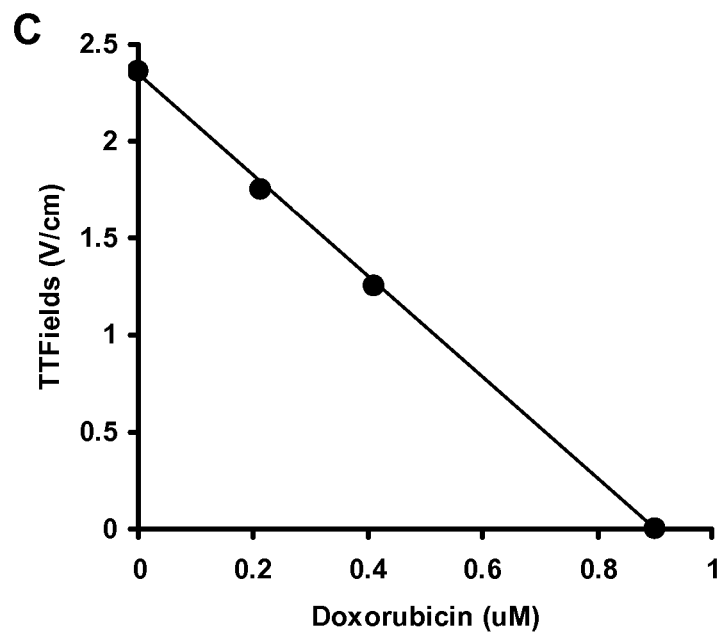
FIG. 11C is an Isobolographic plot for Doxorubicin at different concentrations and TTFields at different intensities on MDA-231 cells.
Figure 11D:
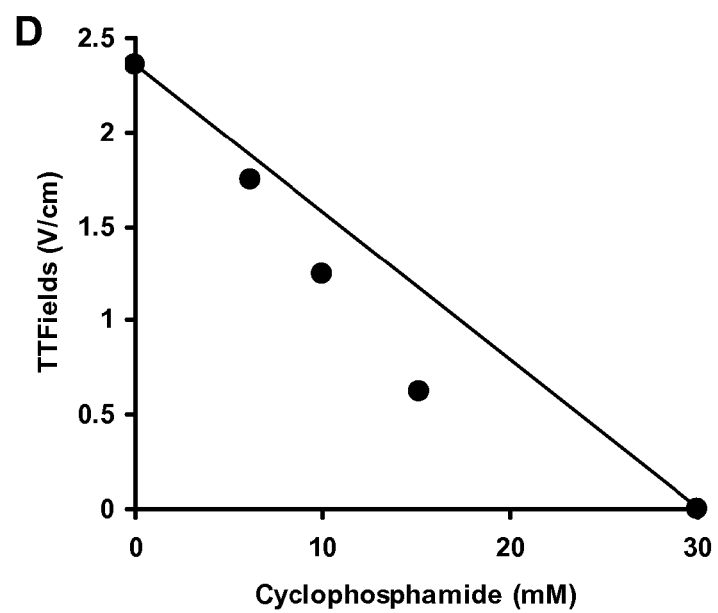
FIG. 11D is an Isobolographic plot for Cyclophosphamide at different concentrations and TTFields at different intensities on MDA-231 cells.

FIG. 11C is an Isobolographic plot for Doxorubicin at different concentrations and TTFields at different intensities on MDA-MB-231 cells; and FIG. 11D is an Isobolographic plot for Cyclophosphamide at different concentrations and TTFields at different intensities on MDA-MB-231 cells. In FIGS. 11C and 11D, the two points on the axes represent the 50% response levels for the respective drug alone and TTFields alone. Note that in all four of the Isobolographic plots (FIGS. 11A-D), the solid line is the linear isobole, and the filled symbols represent responses obtained with combinations.

At high concentrations of Paclitaxel and TTFields intensities, the interaction in breast cancer approaches additivity. One may interpret these findings as an indication that the two agents affect the tubulin and disrupt normal microtubule functions during mitosis in a similar way, but at two different sites or receptors. This conclusion is compatible with the fact that proliferation inhibition by both high concentrations of Paclitaxel (FIG. 8B), and the combined application asymptotically approach complete proliferation arrest. Similar mode of interaction and synergism was observed for Paclitaxel with antitubulin agent, 2-Methoxyestradiol (2-MeO-$E_2$) on MDA-MB-231 cells. Combined treatment with TTFields and Paclitaxel also shows synergistic mode of interaction for non-small lung carcinoma (H1299) cells, but at different TTFields/Paclitaxel ratios as compared to MDA-MB-231 cells. The lung cells show lower sensitivity to Paclitaxel and higher sensitivity to TTFields when applied separately. In combinations, TTFields of lower intensities with Paclitaxel of higher concentrations are required to get synergism between these two treatment modalities.

Doxorubicin (Adriamycin) is an antibiotic that has a broad spectrum of activity both in experimental tumor models and in human malignancy. Table 2 indicates that the combined effect of Doxorubicin and TTFields on MDA-MB-231 cells is additive ($CI_{50}=1$). This result is compatible with the isobolographic analysis of the combination given in FIG. 11C.

The most pronounced synergism was found for the TTFields—Cyclophosphamide combination at the wide range of concentrations. The synergism of the Cyclophosphamide—TTFields combination on the inhibition of MDA-MB-231 cells proliferation is apparent from both Table 2 and FIG. 8D. As seen in FIG. 11D, the synergism increases with Cyclophosphamide concentration, an opposite trend when compared to the concentration dependence of the TTFields—Paclitaxel combination for these cells.

The observed results may be attributable to the mechanism of action of TTFields. Of special significance is the fact that exposure to TTFields for 12 hours or less has no effect on cell proliferation while similar exposure, in combination with Cyclophosphamide, significantly shortens the minimal duration of exposure required to achieve a significant effects. The latency period seen before proliferation is effected, may be due a number of potential mechanisms. The simplest explanation would be the accumulation with time of some active element or elements. In such a case one would expect the effect to increase in time with some linear or exponential kinetics. However, the kinetics seem to be S shaped, i.e. initially (for 12 hours) having no, or very little effect, and then picking up momentum and reaching a steady-state at about 24 hours. The initial segment of such behavior is typical of cooperative or multi-target processes. It is not likely that a 12 hour long delay followed by constant kinetics within an additional period of 12 hours be caused by diffusion processes. Such a behavior may however be the product of a link to the typical 24 hour division cycle of the cell lines involved. Thus, if the TTFields effect on proliferation requires the disruption of two processes ("two hits") that occur at two different points in time that are 12 hours apart in the division cycle, the observed behavior would result. Within this framework the roughly 12 hour delay is the result of the difference in time between the two "hit points" in the cycle. Since the division of the numerous cells involved is not synchronous, it would take an additional period of 12 hours to affect all the dividing cells.

It may be that the unique combined effect of TTFields with Cyclophosphamide results from the fact that the chemical agent, which is present throughout the studied period, disrupts one of the two "hit points" or targets, thus rendering the TTFields effect a regular "single hit" one. The above is consistent, for example, with one target being part of $G_1$ while the other is part of $G_2$. However, there is an indication that TTFields effect the spindle microtubule polymerization—depolymerization stage and Cyclophosphamide effects the S phase. Therefore it is reasonable to assume that one TTFields target is in $G_2$ while the other is part of the S phase where Cyclophosphamide can replace its action.

The results of the experiments reported above support the notion that TTFields may be used as an effective adjunct to enhance the effects of currently used chemotherapeutic agents. This may provide an ideal combination having additive to synergistic efficacy and potentially without an increase in toxicity. Moreover, as seen in FIG. 8 for Cyclophosphamide, the combination with TTFields produces the same therapeutic effect using concentrations of 1 mM, as compared with 30 mM using the drug alone. This dose reduction will most likely result in significantly lower drug side effects. An additional potential benefit is the outcome of the fact that TTFields are physical agent the action of which does not depend on specific cell receptors and thus may be effective over a broad range of malignancies. This wide range efficacy is similar to that of irradiation, but without the severe side effects associated with irradiation. The predicted potential benefits are based on the fact that in pilot clinical trials long term treatment with TTFields was not associated with any significant adverse side effects.

In addition to the five particular drugs discussed above, TTFields can be used in conjunction with other anti-cancer treatments. Examples of other anti-cancer treatments that can be combined with TTFields include, but are not limited to, five general categories:

The first categories is surgery, including but not limited to open surgery, laparoscopic surgery, minimal resection surgery, debulking surgery, complete resection surgery, etc. The second category is local ablation techniques including but not limited to radio-surgery, RF ablation, and focused ultrasound. For these first two categories, the TTFields may be applied before the surgery or ablation to shrink the tumor, and/or after the surgery or ablation to deal with any remains thereof The third category is ionizing radiation using various dosing and focusing regimen including but not limited to whole organ radiation (e.g., brain), regional radiation (e.g. Y shaped), focal radiation, single dose radiation, fractionated dose radiation, and hyper-fractionated dose radiation.

The fourth category is chemotherapy, including but not limited to {a} Alkylating agents that act mainly by forming covalent bonds between DNA bases, including but not limited to Nitrogen Mustards (e.g., Cyclophosphamide), Aziridines and Epoxides (e.g., Thiopeta), Alkyl Sulfonates (e.g. Busulfan), Nitrosureas (e.g., BCNU and CCNU), Hydrazine and Triazine derivatives (e.g., Procarbazine and Temozolomide); {b} Cisplatin and its analogs that act by forming DNA adducts which lead to intra-strand and inter-strand linking leading to the formation of DNA filaments, including but not limited to Carboplatin, Cisplatin, and Oxaliplatin; {c} Antimetabolites including but not limited to Folate metabolism inhibitors (e.g., Methotrexate, Trimetrexate, Tomudex), 5-fluoropyrimidines (e.g., 5-FU), Oral Fluoropyramidines (e.g., Tegafur, Uracil, Capecitabine), Necleoside analogs (e.g., Cytarabine), Gemcitabine, and 6-thiopurines (e.g., 6-MP and 6-TG); {d} Topoisomerase Interactive Agents that affect the topologic states of DNA by interfering or modulating DNA cleavage, strand passage and re-ligation, including but not limited to Epipodophyllotoxins (e.g., Etoposide and Teniposide), Camptothecin Analogs, Anthracyclines (e.g., Doxorubicin, Daunorubicin, Epirubicin, Idarubicin), Mitoxantrone and Losoxantrone, and Dactinomycin; {e} Antimicrotubule Agents, which interfere with the proper polymerization/depolymerization of microtubules, including but not limited to Vinca alkaloids (e.g., Vincristine, Vinorelbine and Vinblastine), Taxanes (e.g., Paclitaxel, Docetaxel), and Estramustine Phosphate; and {f} Numerous miscellaneous agents exist which cannot be classified into any of the above groups, including but not limited to Suramin, Bleomycin, L-Asparaginase, and Amifostine.

The fifth category is biological therapies, including but not limited to {a} Inteferons; {b} Interleukin-2; {c} Hormonal therapies including but not limited to Tamoxifen, Toremifene, Raloxifene, Medroxyprogesterone and Megestrol, Aromatase inhibitors, GNRH analogues, Antiandrogens, Diethylstilbesterol and Estradiol, and Octreotide; {d} Differentiation agents that catalyze the differentiation of cancerous cells into their mature (differentiated) forms and then to programmed cell death, including but not limited to Retinoids (e.g., All-Trans-Retinoic Acid), Arsenic Trioxide, Histone Deacetylase inhibitors, Vitamin D, and Cytokines; {e} Therapeutic Monoclonal Antibodies; and {f} Antiangiogenesis agents (e.g., VEGF inhibitors).

In addition to the in vitro data discussed above, preliminary experiments on live animals with VX2 tumors treated using a combination of Doxil and TTFields show a significant reduction in tumor growth rate for combination therapy as compared to treatment using Doxil alone or TTFields alone. Since TTFields show no systemic toxicities, it appears that TTFields can be applied to patients before, during and/or after any other anti-cancer treatment to combat the cancer using two different modalities. The dosages, strengths, and timing of the various treatments may be changed to optimize the results that are desired. Note that the most beneficial combination regimen may differ considerably depending on the type of cancer treated, the exact stage of the disease and the type of anticancer treatment used, it should be relatively simple to determine the best combination regimen experimentally. TTFields can also be applied together with more than one of the other anti-cancer approaches.

Figure 12:
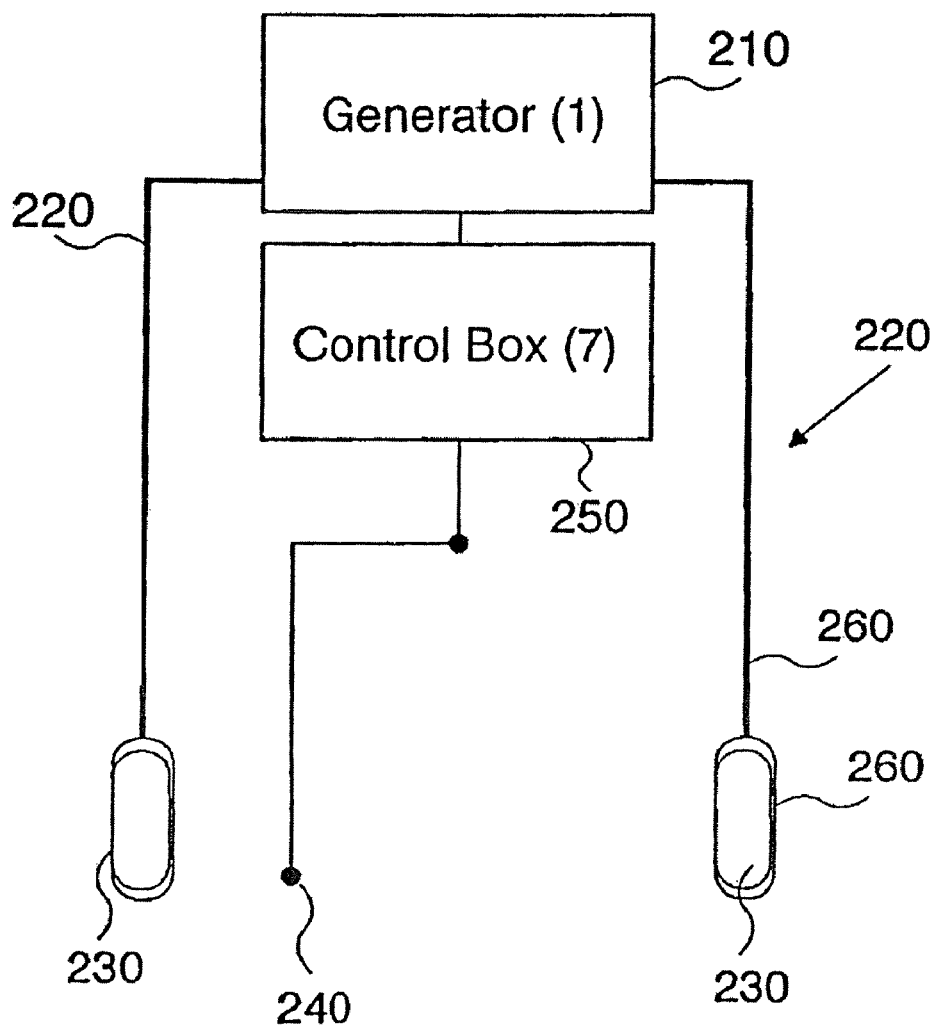
FIG. 12 is a schematic block diagram of an apparatus for applying an electric according to one exemplary embodiment for selectively destroying cells.

FIG. 12 is an example of an apparatus that is suitable for use in treating live patients with combined TTField and drug therapy, and it may be used in combination with any conventional drug delivery mechanism (not shown) to implement the combined TTField and drug therapy. FIG. 12 is a simple schematic diagram of the electronic apparatus 200 illustrating the major components thereof. The electronic apparatus 200 generates the desired electric waveforms. The apparatus 200 includes a generator 210 and a pair of conductive leads 220 that are attached at one end thereof to the generator 210. The opposite ends of the leads 220 are connected to insulated conductors 230 that are activated by the electric signals (e.g., waveforms). The insulated conductors 230 are also referred to hereinafter as isolects 230. Optionally and according to another exemplary embodiment, the apparatus 200 includes a temperature sensor 240 and a control box 250 which are both added to control the amplitude of the electric field generated so as not to generate excessive heating in the area that is treated.

The generator 210 generates an alternating voltage waveform at frequencies in the range from about 50 KHz to about 500 KHz (preferably from about 100 KHz to about 300 KHz). The required voltages are such that the electric field intensity in the tissue to be treated is in the range of about 0.1 V/cm to about 10 V/cm, and preferable between about 1 V/cm and about 5 V/Cm. To achieve this field, the actual potential difference between the two conductors in the isolects 230 is determined by the relative impedances of the system components, as described below.

When the control box 250 is included, it controls the output of the generator 210 so that it will remain constant at the value preset by the user or the control box 250 sets the output at the maximal value that does not cause excessive heating, or the control box 250 issues a warning or the like when the temperature (sensed by temperature sensor 240) exceeds a preset limit.

The leads 220 are standard isolated conductors with a flexible metal shield, preferably grounded so that it prevents the spread of the electric field generated by the leads 220. The isolects 230 have specific shapes and positioning so as to generate an electric field of the desired configuration, direction and intensity at the target volume and only there so as to focus the treatment.

The specifications of the apparatus 200 as a whole and its individual components are largely influenced by the fact that at the frequency of the TTFields (50 KHz-500 KHz), living systems behave according to their "Ohmic", rather than their dielectric properties. The only elements in the apparatus 200 that behave differently are the insulators of the isolects 230 (see FIGS. 14-15). The isolects 200 consist of a conductor in contact with a dielectric that is in contact with the conductive tissue thus forming a capacitor.

Figure 13:
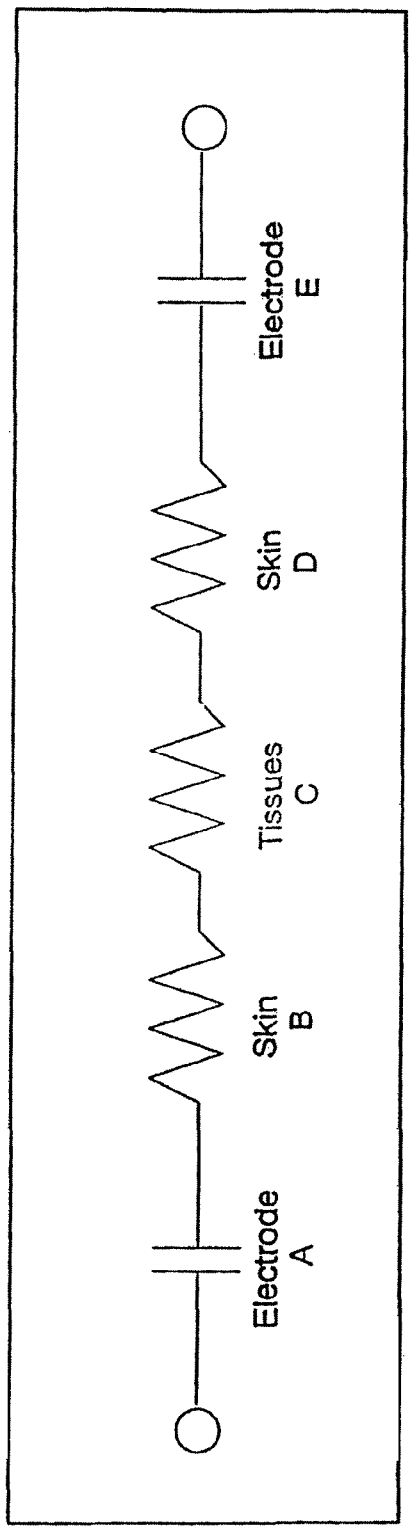
FIG. 13 is a simplified schematic diagram of an equivalent electric circuit of insulated electrodes of the apparatus of FIG. 12.

The details of the construction of the isolects 230 is based on their electric behavior that can be understood from their simplified electric circuit when in contact with tissue as generally illustrated in FIG. 13. In the illustrated arrangement, the potential drop or the electric field distribution between the different components is determined by their relative electric impedance, i.e., the fraction of the field on each component is given by the value of its impedance divided by the total circuit impedance. For example, the potential drop on element ? $V_A=A/(A+B+C+D+E)$. Thus, for DC or low frequency AC, practically all the potential drop is on the capacitor (that acts as an insulator). For relatively very high frequencies, the capacitor practically is a short and therefore, practically all the field is distributed in the tissues. At the frequencies of the TTFields (e.g., 50 KHz to 500 KHz), which are intermediate frequencies, the impedance of the capacitance of the capacitors is dominant and determines the field distribution. Therefore, in order to increase the effective voltage drop across the tissues (field intensity), the impedance of the capacitors is to be decreased (i.e., increase their capacitance). This can be achieved by increasing the effective area of the "plates" of the capacitor, decrease the thickness of the dielectric or use a dielectric with high dielectric constant.

In order to optimize the field distribution, the isolects 230 are configured differently depending upon the application in which the isolects 230 are to be used. There are two principle modes for applying the TTFields. First, the TTFields can be applied by external isolects and second, the TTFields can be applied by internal isolects.

Figure 14:
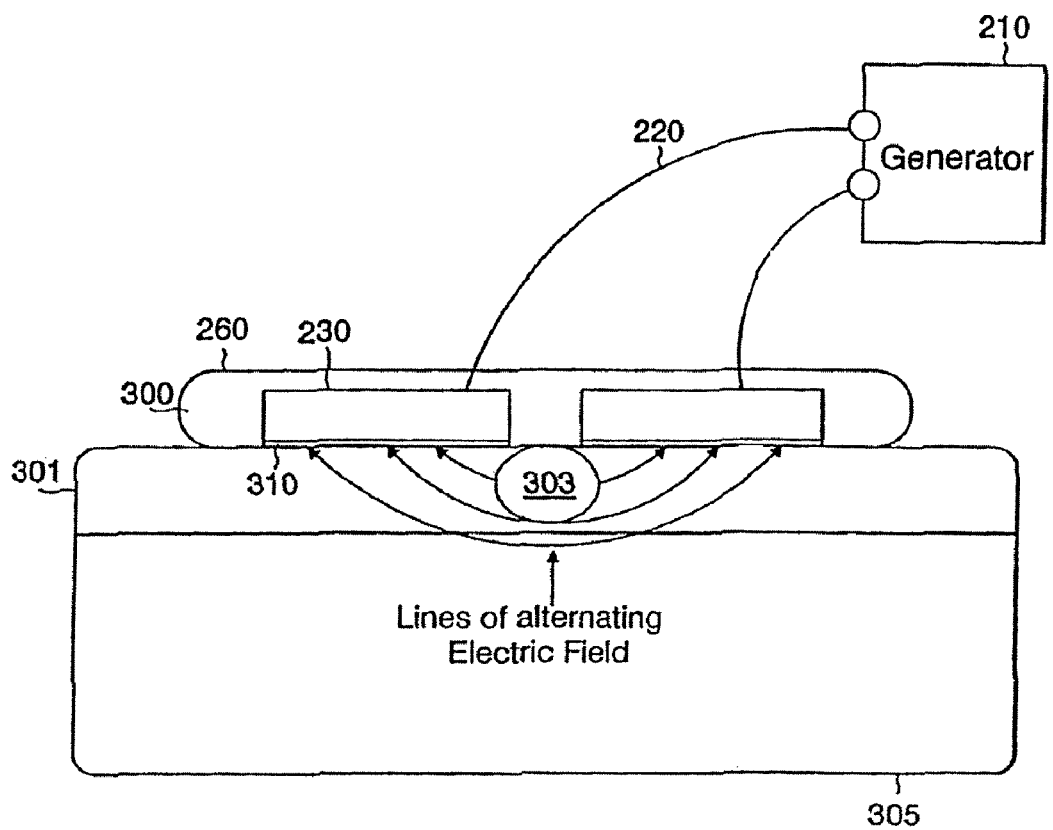

TTFields that are applied by external isolects can be of a local type or widely distributed type. The first type includes, for example, the treatment of skin tumors and treatment of lesions close to the skin surface. FIG. 14 illustrates an exemplary embodiment where the isolects 230 are incorporated in a skin patch 300. The skin patch 300 can be a self-adhesive flexible patch with one or more pairs of isolects 230. The patch 300 includes internal insulation 310 (formed of a dielectric material) and the external insulation 260 and is applied to skin surface 301 that contains a tumor 303 either on the skin surface 301 or slightly below the skin surface 301. Tissue is generally indicated at 305. To prevent the potential drop across the internal insulation 310 to dominate the system, the internal insulation 310 must have a relatively high capacity. This can be achieved by a large surface area; however, this may not be desired as it will result in the spread of the field over a large area (e.g., an area larger than required to treat the tumor). Alternatively, the internal insulation 310 can be made very thin and/or the internal insulation 310 can be of a high dielectric constant. As the skin resistance between the electrodes (labeled as A and E in FIG. 13) is normally significantly higher than that of the tissue (labeled as C in FIG. 13) underneath it (1-10 KO vs. 0.1-1 KO), most of the potential drop beyond the isolects occurs there. To accommodate for these impedances (Z), the characteristics of the internal insulation 310 (labeled as B and D in FIG. 13) should be such that they have impedance preferably under 100 KO at the frequencies of the TTFields (e.g., 50 KHz to 500 KHz). For example, if it is desired for the impedance to be about 10 K Ohms or less, such that over 1% of the applied voltage falls on the tissues, for isolects with a surface area of 10 mm$^2$, at frequencies of 200 KHz, the capacity should be on the order of $10^{-10}$ F., which means that using standard insulations with a dielectric constant of 2-3, the thickness of the insulating layer 310 should be about 50-100 microns. An internal field 10 times stronger would be obtained with insulators with a dielectric constant of about 20-50.

Using an insulating material with a high dielectric constant increases the capacitance of the electrodes, which results in a reduction of the electrodes' impedance to the AC signal that is applied by the generator 1 (shown in FIG. 12). Because the electrodes A, E are wired in series with the target tissue C, as shown in FIG. 13, this reduction in impedance reduces the voltage drop in the electrodes, so that a larger portion of the applied AC voltage appears across the tissue C. Since a larger portion of the voltage appears across the tissue, the voltage that is being applied by the generator 1 can be advantageously lowered for a given field strength in the tissue.

The desired field strength in the tissue being treated is preferably between about 0.1 V/cm and about 10 V/cm, and more preferably between about 2 V/cm and 3 V/cm or between about 1 V/cm and about 5 V/cm. If the dielectric constant used in the electrode is sufficiently high, the impedance of the electrodes A, E drops down to the same order of magnitude as the series combination of the skin and tissue B, C, D. One example of a suitable material with an extremely high dielectric constant is $CaCu_3Ti_4O_{12}$, which has a dielectric constant of about 11,000 (measured at 100 kHz). When the dielectric constant is this high, useful fields can be obtained using a generator voltage that is on the order of a few tens of Volts.

Since the thin insulating layer can be very vulnerable, etc., the insulation can be replaced by very high dielectric constant insulating materials, such as titanium dioxide (e.g., rutile), the dielectric constant can reach values of about 200. There a number of different materials that are suitable for use in the intended application and have high dielectric constants. For example, some materials include: lithium niobate ($LiNbO_3$), which is a ferroelectric crystal and has a number of applications in optical, pyroelectric and piezoelectric devices; yttrium iron garnet (YIG) is a ferromagnetic crystal and magneto-optical devices, e.g., optical isolator can be realized from this material; barium titanate ($BaTiO_3$) is a ferromagnetic crystal with a large electro-optic effect; potassium tantalate ($KTaO_3$) which is a dielectric crystal (ferroelectric at low temperature) and has very low microwave loss and tunability of dielectric constant at low temperature; and lithium tantalate ($LiTaO_3$) which is a ferroelectric crystal with similar properties as lithium niobate and has utility in electro-optical, pyroelectric and piezoelectric devices. Insulator ceramics with high dielectric constants may also be used, such as a ceramic made of a combination of Lead Magnesium Niobate and Lead Titanate. It will be understood that the aforementioned exemplary materials can be used in combination with the present device where it is desired to use a material having a high dielectric constant.

Figure 16:
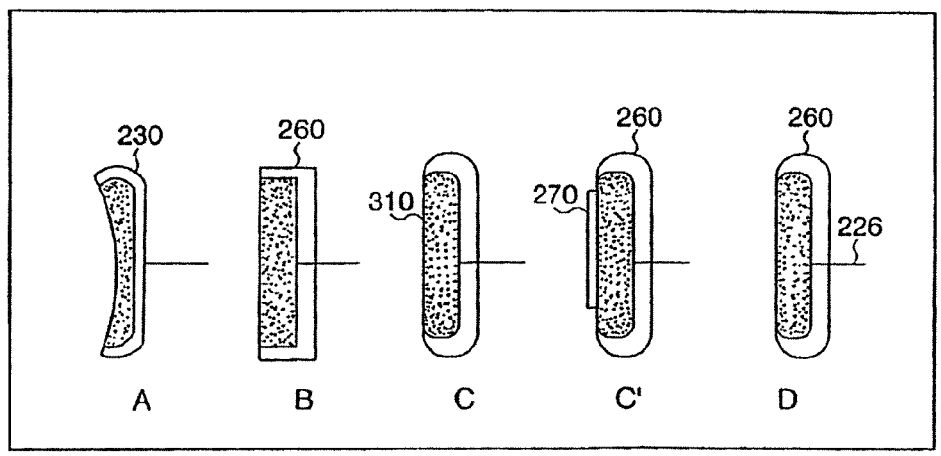
FIGS. 16A-16D are cross-sectional illustrations of various constructions of the insulated electrodes of the apparatus of FIG. 12.

One must also consider another factor that affects the effective capacity of the isolects 230, namely the presence of air between the isolects 230 and the skin. Such presence, which is not easy to prevent, introduces a layer of an insulator with a dielectric constant of 1.0, a factor that significantly lowers the effective capacity of the isolects 230 and neutralizes the advantages of the titanium dioxide (rutile), etc. To overcome this problem, the isolects 230 can be shaped so as to conform with the body structure and/or (2) an intervening filler 270 (as illustrated in FIG. 16C), such as a gel, that has high conductance and a high effective dielectric constant, can be added to the structure. The shaping can be pre-structured (see FIG. 16A) or the system can be made sufficiently flexible so that shaping of the isolects 230 is readily achievable. The gel can be contained in place by having an elevated rim as depicted in FIGS. 16C and 16C'. The gel can be made of hydrogels, gelatins, agar, etc., and can have salts dissolved in it to increase its conductivity. FIGS. 16A-16C' illustrate various exemplary configurations for the isolects 230. The exact thickness of the gel is not important so long as it is of sufficient thickness that the gel layer does not dry out during the treatment. In one exemplary embodiment, the thickness of the gel is about 0.5 mm to about 2 mm. Preferably, the gel has high conductivity, is tacky, and is biocompatible for extended periods of time. One suitable gel is AG603 Hydrogel, which is available from AmGel Technologies, 1667 S. Mission Road, Fallbrook, Calif. 92028-4115, USA.

In order to achieve the desirable features of the isolects 230, the dielectric coating of each should be very thin, for example from between 1-50 microns. Since the coating is so thin, the isolects 230 can easily be damaged mechanically or undergo dielectric breakdown. This problem can be overcome by adding a protective feature to the isolect's structure so as to provide desired protection from such damage. Examples of some suitable protective features are described in published application US2005/0209642, which is incorporated herein by reference.

However, the capacity is not the only factor to be considered. The following two factors also influence how the isolects 230 are constructed. The dielectric strength of the internal insulating layer 310 and the dielectric losses that occur when it is subjected to the TTFields, i.e., the amount of heat generated. The dielectric strength of the internal insulation 310 determines at what field intensity the insulation will be "shorted" and cease to act as an intact insulation. Typically, insulators, such as plastics, have dielectric strength values of about 100V per micron or more. As a high dielectric constant reduces the field within the internal insulator 310, a combination of a high dielectric constant and a high dielectric strength gives a significant advantage. This can be achieved by using a single material that has the desired properties or it can be achieved by a double layer with the correct parameters and thickness. In addition, to further decreasing the possibility that the insulating layer 310 will fail, all sharp edges of the insulating layer 310 should be eliminated as by rounding the corners, etc., as illustrated in FIG. 16D using conventional techniques.

Figure 15:
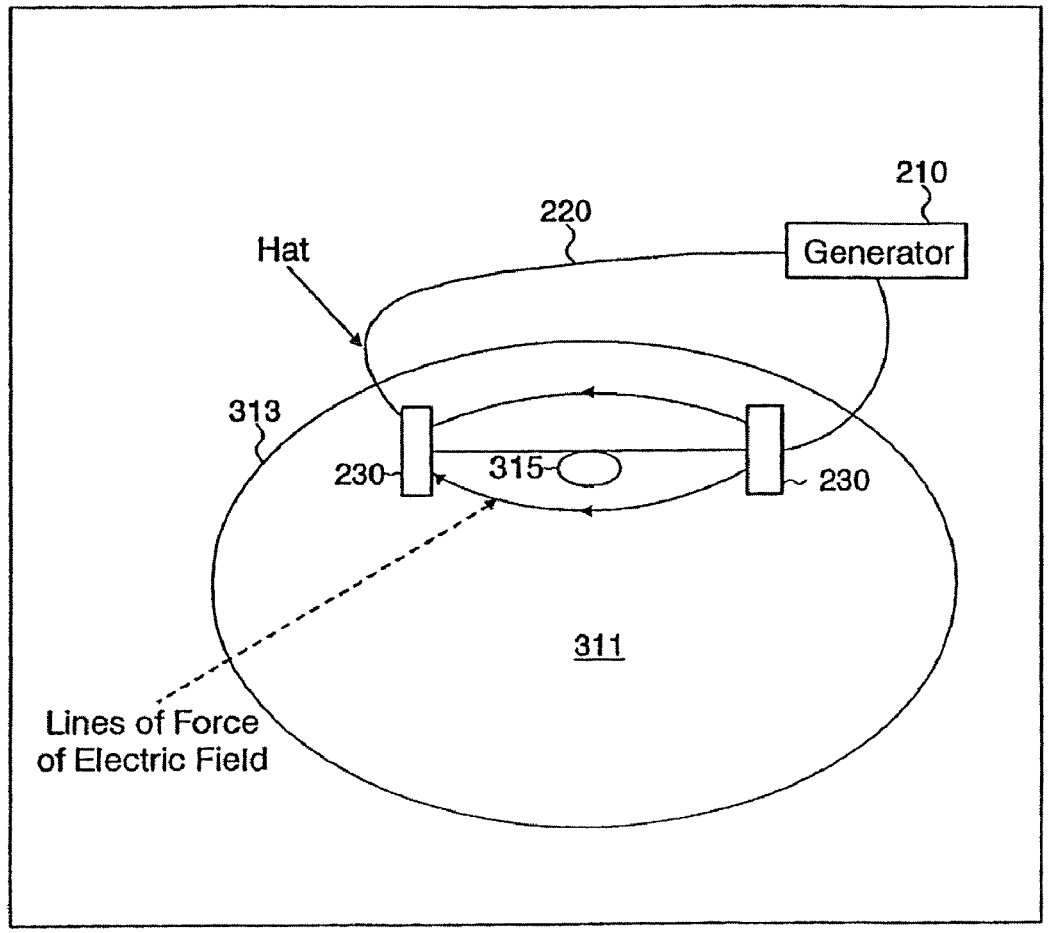

FIG. 15 illustrates a second type of treatment using the isolects 230, namely electric field generation by internal isolects 230. A body to which the isolects 230 are implanted is generally indicated at 311 and includes a skin surface 313 and a tumor 315. In this embodiment, the isolects 230 can have the shape of plates, wires or other shapes that can be inserted subcutaneously or a deeper location within the body 311 so as to generate an appropriate field at the target area (tumor 315).

Figure 17:
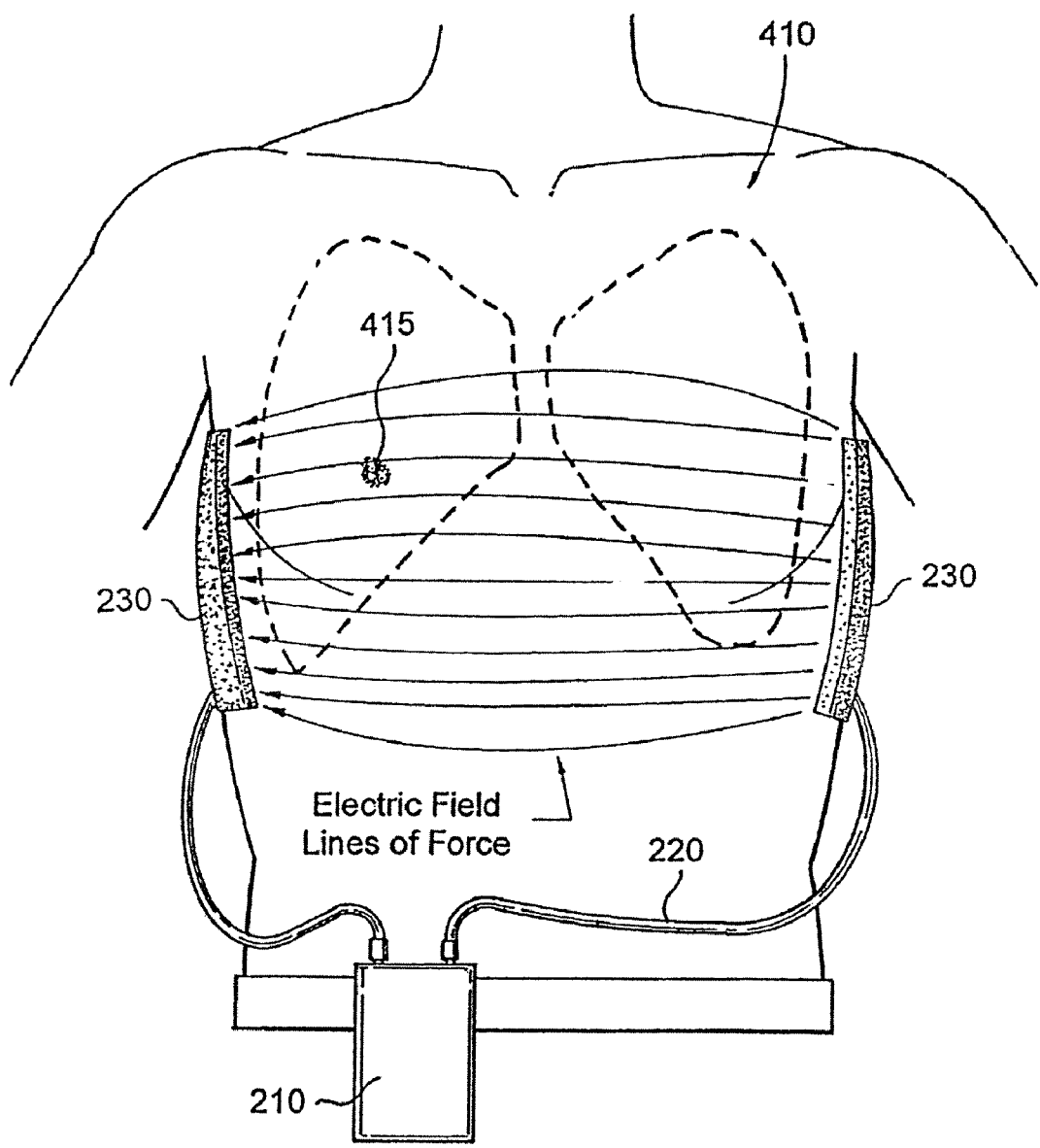
FIG. 17 is a front elevational view in partial cross-section of two insulated electrodes being arranged about a human torso for treatment of a tumor container within the body, e.g., a tumor associated with lung cancer.

It will also be appreciated that the mode of isolects application is not restricted to the above descriptions. In the case of tumors in internal organs, for example, liver, lung, etc., the distance between each member of the pair of isolects 230 can be large. The pairs can even by positioned opposite sides of a torso 410, as illustrated in FIG. 17. The arrangement of the isolects 230 in FIG. 17 is particularly useful for treating a tumor 415 associated with lung cancer or gastrointestinal tumors. In this embodiment, the TTFields spread in a wide fraction of the body. Note also that in addition to external electrode embodiments described above, the combined TTField and drug treatment may be implemented using the internal probe embodiments described in published application US2005/0209642, which is incorporated herein by reference.

In order to avoid overheating of the treated tissues, a selection of materials and field parameters is needed. The isolects insulating material should have minimal dielectric losses at the frequency ranges to be used during the treatment process. This factor can be taken into consideration when choosing the particular frequencies for the treatment. The direct heating of the tissues will most likely be dominated by the heating due to current flow (given by the I*R product). In addition, the isolect (insulated electrode) 230 and its surroundings should be made of materials that facilitate heat losses and its general structure should also facilitate head losses, i.e., minimal structures that block heat dissipation to the surroundings (air) as well as high heat conductivity. Using larger electrodes also minimizes the local sensation of heating, since it spreads the energy that is being transferred into the patient over a larger surface area. Preferably, the heating is minimized to the point where the patient's skin temperature never exceeds about 39° C.

Another way to reduce heating is to apply the field to the tissue being treated intermittently, by applying a field with a duty cycle between about 20% and about 50% instead of using a continuous field. For example, to achieve a duty cycle of 33%, the field would be repetitively switched on for one second, then switched off for two seconds. Preliminary experiments have shown that the efficacy of treatment using a field with a 33% duty cycle is roughly the same as for a field with a duty cycle of 100%. In alternative embodiments, the field could be switched on for one hour then switched off for one hour to achieve a duty cycle of 50%. Of course, switching at a rate of once per hour would not help minimize short-term heating. On the other hand, it could provide the patient with a welcome break from treatment.

It will also be appreciated that the present apparatus can further include a device for rotating the TTFields relative to the living tissue. For example and according to one embodiment, the alternating electric potential applies to the tissue being treated is rotated relative to the tissue using conventional devices, such as a mechanical device that upon activation, rotates various components of the present system.

The TTFields may be applied to different pairs of the insulated electrodes 230 in a consecutive manner in order to vary the direction of the TTFields that travel through the target region, as described in published application US2005/0209642, which is incorporated herein by reference. The changing of the field's direction may be implemented in a stepwise manner or in a continuous manner, also as described in published application US2005/0209642.

As described in published application US2005/0209642, it can be advantageous to apply a distribution of different frequencies to the population. For example, experiments indicate that using two frequencies of 170 kHz and 250 kHz to destroy a population of glioma cells would be more effective than using a single frequency of 200 kHz. When more than one frequency is used, the various frequencies may be applied sequentially in time. For example, in the case of glioma, field frequencies of 100, 150, 170, 200, 250, and 300 kHz may be applied during the first, second, third, fourth, fifth, and sixth minutes of treatment, respectively. That cycle of frequencies would then repeat during each successive six minutes of treatment. Alternatively, the frequency of the field may be swept in a stepless manner from 100 to 300 kHz. Optionally, this frequency cycling may be combined with the directional changes described above.

In an alternative embodiment, a signal that contains two or more frequencies components simultaneously (e.g., 170 kHz and 250 kHz) is applied to the electrodes to treat a populations of cells that have a distribution of sizes. The various signals will add by superposition to create a field that includes all of the applied frequency components.

As used herein, the term "tumor" refers to a malignant tissue comprising transformed cells that grow uncontrollably. In addition, the present invention can control uncontrolled growth associated with non-malignant or pre-malignant conditions, and other disorders involving inappropriate cell or tissue growth by application of an electric field in accordance with the invention to the tissue undergoing inappropriate growth.

Furthermore, undesirable fibroblast and endothelial cell proliferation associated with wound healing, leading to scar and keloid formation after surgery or injury, and restenosis after angioplasty or placement of coronary stents can be inhibited by application of an electric field in accordance with the present invention. The non-invasive nature of this invention makes it particularly desirable for these types of conditions, particularly to prevent development of internal scars and adhesions, or to inhibit restenosis of coronary, carotid, and other important arteries.

Thus, the present invention provides an effective, simple method of selectively destroying dividing cells, e.g., tumor cells and parasitic organisms, while non-dividing cells or organisms are left affected by application of the method on living tissue containing both types of cells or organisms. Thus, unlike many of the conventional methods, the present invention does not damage the normal cells or organisms. In addition, the present invention does not discriminate based upon cell type (e.g., cells having differing sizes) and therefore may be used to treat any number of types of sizes having a wide spectrum of characteristics, including varying dimensions.

While the invention has been particularly shown and described with reference to preferred embodiments thereof, it will be understood by those skilled in the art that various changes in form and details can be made without departing from the spirit and scope of the invention.

I claim:

1. A method of killing or inhibiting the growth of cancer cells in a target region, the method comprising the steps of:
    applying, to the target region, an AC electric field that damages the cancer cells or inhibits the growth of the cancer cells, but leaves normal cells in the target region substantially unharmed, wherein the electric field has a frequency between 50 kHz and 500 kHz and wherein the direction of the field is changed in an alternating sequence by applying the field between different sets of electrodes; and
    treating the cancer cells with an other anti-cancer regimen, wherein the applying step and the treating step are performed simultaneously.

2. The method of claim 1, wherein the other anti-cancer regimen comprises treating the cancer cells with an anti-cancer drug.

3. A method of killing or inhibiting the growth of cancer cells in a target region, the method comprising the steps of:
    applying, to the target region, an electric field that damages the cancer cells or inhibits the growth of the cancer cells, but leaves normal cells in the target region substantially unharmed; and
    treating the cancer cells with an anti-cancer drug, wherein the applying step and the treating step are performed simultaneously, and wherein the drug comprises at least one of Paclitaxel, Doxorubicin, Cyclophosphamide, and Cisplatin.

4. A method of killing or inhibiting the growth of cancer cells in a target region, the method comprising the steps of:
    applying, to the target region, an electric field that damages the cancer cells or inhibits the growth of the cancer cells, but leaves normal cells in the target region substantially unharmed; and
    treating the cancer cells with an anti-cancer drug, wherein the applying step and the treating step are performed simultaneously, and wherein the drug dosage is less than 20% of a standard dosage for the drug.

5. A method of inhibiting the growth of cancer cells in a target region, the method comprising the steps of:
    treating the cancer cells with an anti-cancer drug; and
    applying an AC electric field to the target region for a period of time, wherein the electric field has frequency and field strength characteristics selected to inhibit the growth of cancer cells in the target region and wherein the electric field has a frequency between 50 kHz and 500 kHz and wherein the direction of the field is changed in an alternating sequence by applying the field between different sets of electrodes.

6. A method of inhibiting the growth of cancer cells in a target region, the method comprising the steps of:
    treating the cancer cells with an anti-cancer drug; and
    applying an electric field to the target region for a period of time, wherein the electric field has frequency and field strength characteristics selected to inhibit the growth of cancer cells in the target region, and
    wherein the drug dosage is less than 20% of a standard dosage for the drug.

7. The method of claim 5, wherein the period of time is at least 24 hours.

8. The method of claim 5, wherein the field strength is at least 1 V/cm.

9. A method of inhibiting the growth of cancer cells in a target region, the method comprising the steps of:
    treating the cancer cells with an anti-cancer drug; and
    applying an AC electric field to the target region for a period of time, wherein the electric field has frequency and field strength characteristics selected to inhibit the growth of cancer cells in the target region, and
    wherein the drug comprises at least one of Paclitaxel, Doxorubicin, Cyclophosphamide, and Cisplatin.

10. The method of claim 9, wherein the field strength of the electric field is at least 1 V/cm and the period of time is at least 24 hours.

11. The method of claim 10, wherein the frequency of the electric field is about 150 kHz.

12. The method of claim 10, wherein the frequency of the electric field is about 200 kHz.

13. A method of killing or inhibiting the growth of cancer cells in a target region, the method comprising the step of
    Applying, an AC electric field that damages the cancer cells or inhibits the growth of the cancer cells, but leaves normal cells in the target region substantially unharmed, wherein the AC electric field is applied while the cancer cells are being treated with an anti-cancer drug, wherein the electric field has frequency between about 100 kHz and 300 kHz, and a field strength in the target region of at least 1 V/cm and wherein the direction of the field is changed in an alternating sequence by applying the field between different sets of electrodes.

14. The method of claim 13, wherein the drug comprises Cyclophosphamide.

15. The method of claim 14, wherein the period of time is at least 6 hours.

16. The method of claim 15, wherein the frequency is about 150 kHz.

17. The method of claim 15, wherein the frequency is about 200 kHz.

18. The method of claim 13, wherein the drug dosage is less than 20% of a standard dosage for the drug.

19. The method of claim 13, wherein the period of time is at least 24 hours.

20. The method of claim 13, wherein the drug comprises at least one of Paclitaxel, Doxorubicin, Cyclophosphamide, and Cisplatin.

21. The method of claim 13, wherein the field strength is between 1 V/cm and 5 V/cm and the period of time is at least 24 hours.

22. The method of claim 21, wherein the frequency is about 150 kHz.

23. The method of claim 21, wherein the frequency is about 200 kHz.

* * * * *

UNITED STATES PATENT AND TRADEMARK OFFICE
CERTIFICATE OF CORRECTION

| | |
|---|---|
| PATENT NO. | : 8,019,414 B2 |
| APPLICATION NO. | : 11/695176 |
| DATED | : September 13, 2011 |
| INVENTOR(S) | : Yoram Palti |

It is certified that error appears in the above-identified patent and that said Letters Patent is hereby corrected as shown below:

Column 20, line 63, change "Applying" to --applying, to the target region--.

Signed and Sealed this
Twenty-ninth Day of November, 2011

David J. Kappos
*Director of the United States Patent and Trademark Office*